United States Patent [19]

Fukuma et al.

[11] Patent Number: 5,071,245
[45] Date of Patent: Dec. 10, 1991

[54] OCULAR REFRACTING POWER MEASURING SYSTEM

[75] Inventors: Yasufumi Fukuma; Akio Umeda; Ikuo Kitao; Noriyuki Nagai; Yasuhisa Ishikura; Kazutoshi Uchida, all of Tokyo, Japan

[73] Assignee: Kabushiki Kaisha TOPCON, Tokyo, Japan

[21] Appl. No.: 443,111

[22] Filed: Nov. 29, 1989

[30] Foreign Application Priority Data

| Dec. 6, 1988 | [JP] | Japan | 63-308314 |
| Dec. 6, 1988 | [JP] | Japan | 63-308315 |
| Mar. 27, 1989 | [JP] | Japan | 1-74183 |
| Mar. 27, 1989 | [JP] | Japan | 1-74184 |
| Mar. 27, 1989 | [JP] | Japan | 1-74185 |
| Mar. 27, 1989 | [JP] | Japan | 1-74188 |
| Mar. 27, 1989 | [JP] | Japan | 1-74189 |
| Mar. 27, 1989 | [JP] | Japan | 1-74190 |
| Apr. 5, 1989 | [JP] | Japan | 1-86101 |
| Apr. 5, 1989 | [JP] | Japan | 1-86103 |
| Apr. 5, 1989 | [JP] | Japan | 1-86105 |
| Apr. 5, 1989 | [JP] | Japan | 1-86107 |
| Jun. 22, 1989 | [JP] | Japan | 1-160083 |

[51] Int. Cl.$^5$ .............................................. A61B 3/00
[52] U.S. Cl. ..................................... 351/211; 351/205
[58] Field of Search ................ 351/205, 211, 212, 214

[56] References Cited

U.S. PATENT DOCUMENTS

| 4,293,198 | 10/1981 | Kohayakawa et al. | 351/211 |
| 4,306,778 | 12/1981 | Wada et al. | 351/211 |
| 4,376,573 | 3/1983 | Matsumura et al. | 351/214 |
| 4,878,750 | 11/1989 | Sekiguchi | 351/205 |
| 4,952,049 | 8/1990 | Matsumoto | 351/205 |

Primary Examiner—Rodney B. Bovernick
Assistant Examiner—J. P. Ryan
Attorney, Agent, or Firm—Nields & Lemack

[57] ABSTRACT

An ocular refracting power measuring system includes a projector system for projecting the image of a light source on the eyeground of an eye to be tested and a light receiving system for condensing the light beam from the eyeground onto a light receiving element disposed at a position substantially conjugate with the pupil of the eye to be tested, whereby the ocular refracting power of the eye to be tested can be measured based on the distribution of light amount on the light receiving element and variations of the distribution of light amount due to the changed amount of light in the light source.

26 Claims, 31 Drawing Sheets

FIG.I(A)
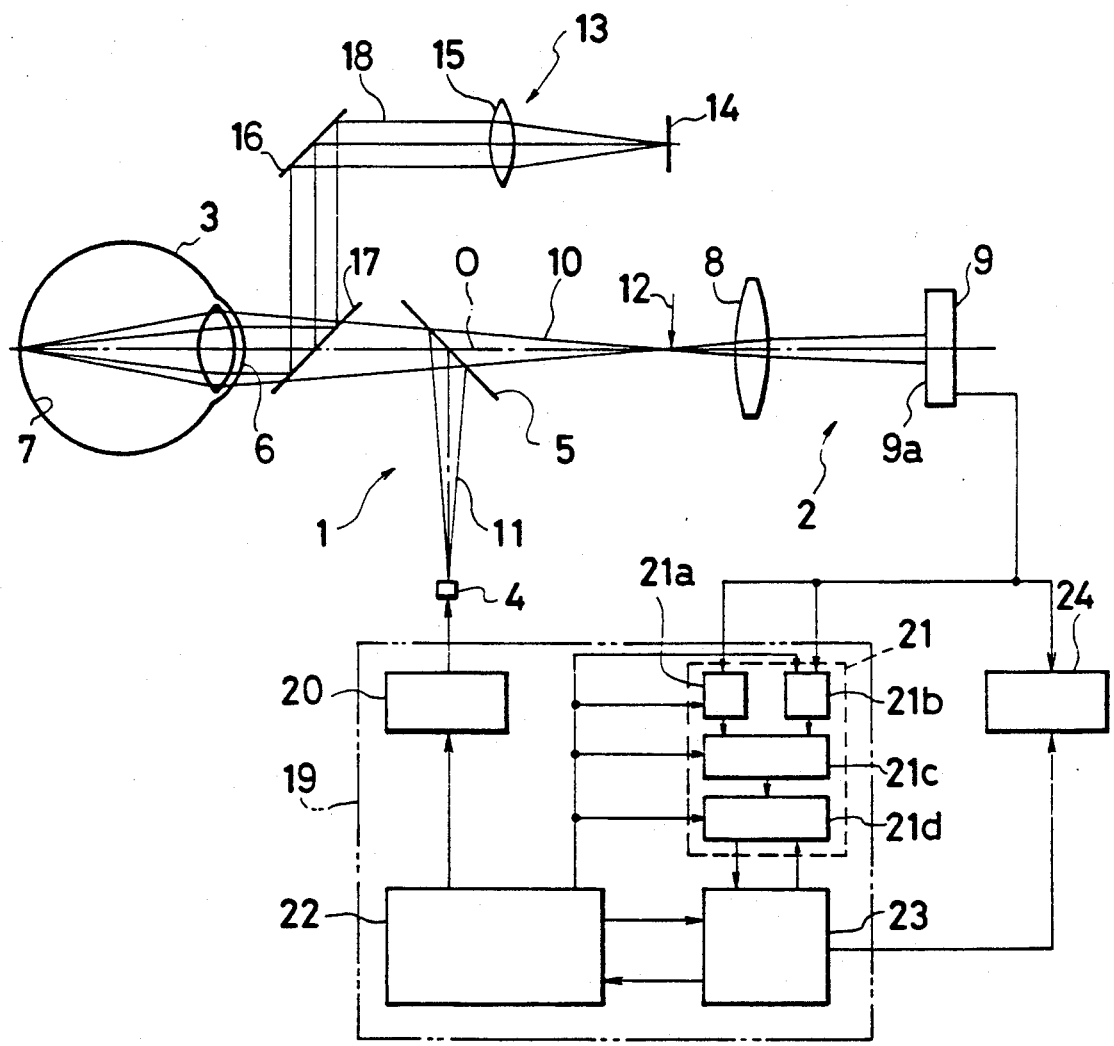

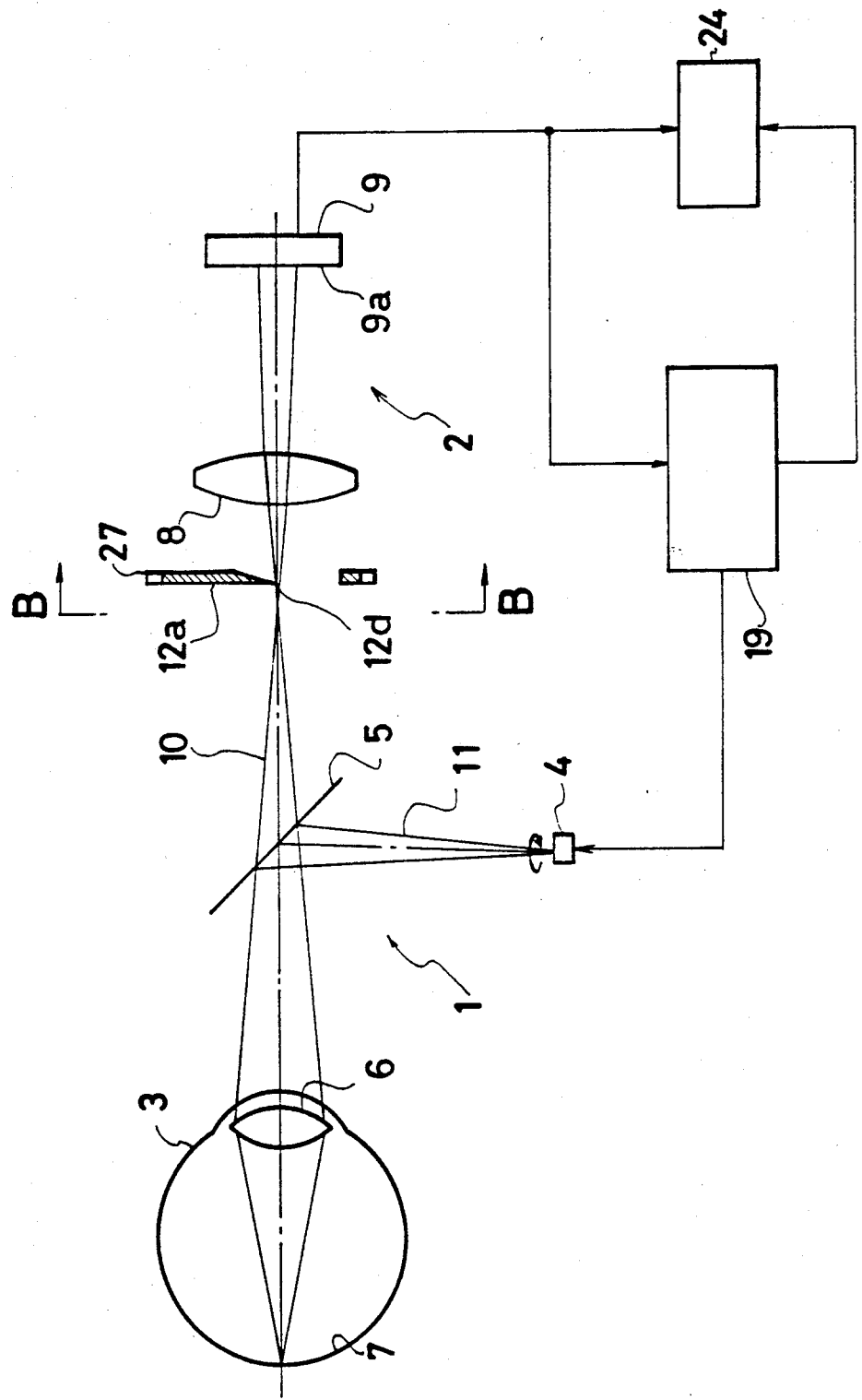

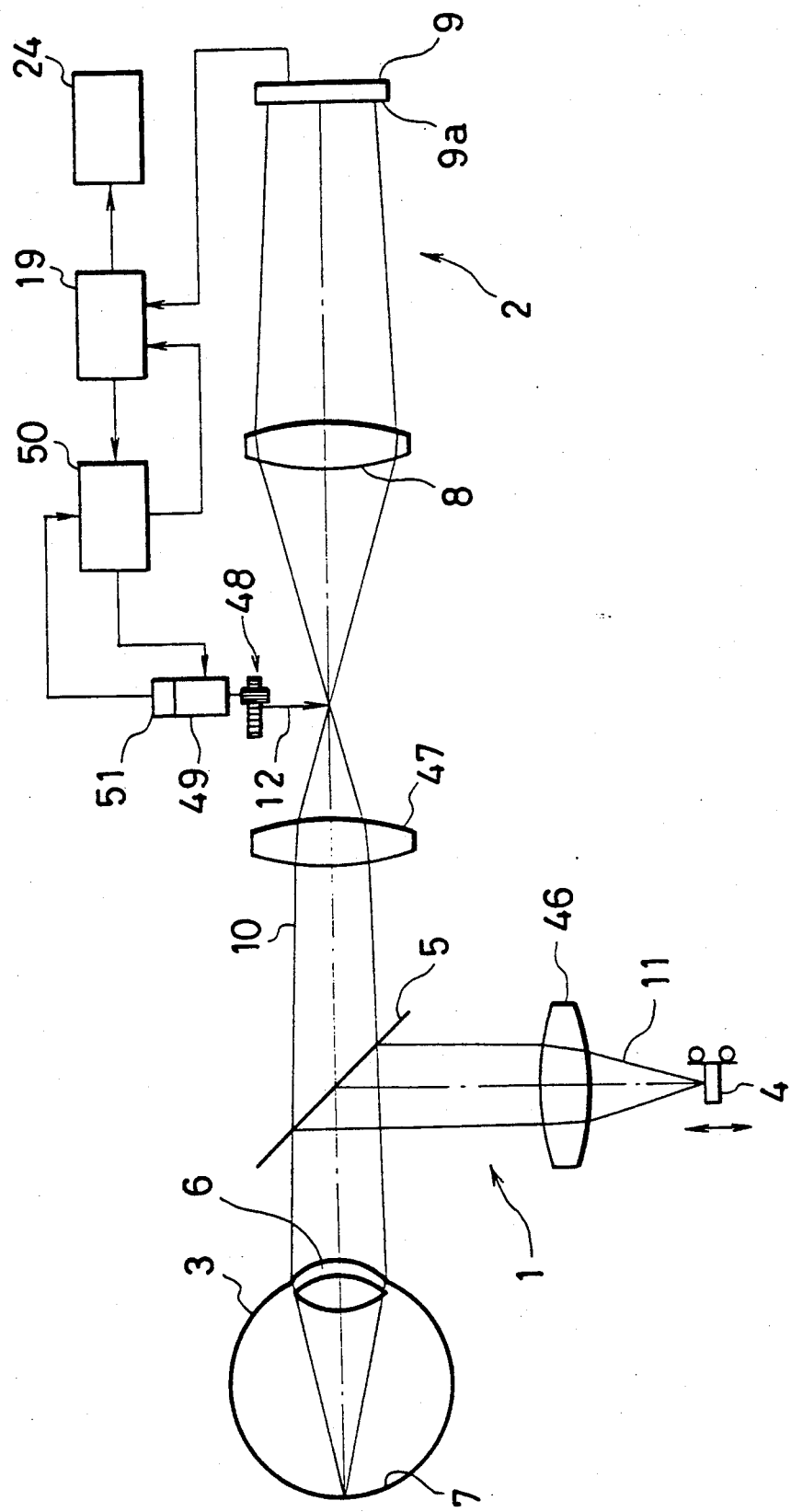

5,071,245

OCULAR REFRACTING POWER MEASURING SYSTEM

BACKGROUND OF THE INVENTION

1. Field of the Invention

The present invention relates to an ocular refracting power measuring system which is particularly useful for infants and even for babies.

2. Description of the Related Art

There are known ocular refracting power measuring systems which include a so-called subjective type ophthalmoscope for measuring the ocular refracting power of a patient in accordance with his response, a so-called auto-refractomer for objectively measuring the ocular refracting power and so on.

When it is to measure the ocular refracting power of babies using such types of systems, the subjective type opthalmoscope cannot measure it since cooperation from the babies cannot be obtained. The general auto-refractometer is extremely difficult to measure the ocular refracting power of babies since they cannot easily be fixed in position relative to the auto-refractometer.

In order to overcome such defects, there has been proposed a so-called photo-refraction type measuring process which consists of illuminating the eyeground of a patient by the use of a strobo flash, photographing the state of the beam at the pupil of the patient and determining the refracting power from the photographed result.

It was believed that the photo-refraction type measuring process was useful in measuring the ocular refracting power of babies since the measurement can be sufficiently performed even if the optical axis of the eye to be tested was deflected slightly out of the normal measurement axis.

In the ocular refracting power measuring system of the photo-refraction type, the beam of stroboscopic light is directed slantly to the optical axis of the camera so that only the image of the pupil will be photographed. However, there are values of diopter which cannot be measured by the position of the light source. The photo-refraction type system also has a problem in that it can measure the ocular refracting power only within a reduced range of measurement.

SUMMARY OF THE INVENTION

It is therefore an object of the present invention to provide an ocular refracting power measuring system which can measure any diopter and also provide the result instantaneously.

Another object of the present invention is to provide an ocular refracting power measuring system which can measure an ocular refracting power in a more accurate manner without affection of any external light.

Still another object of the present invention is to provide an ocular refracting power measuring system which can measure an ocular refracting power as well as the degree of astigmatism and the angle of astigmatic axis.

A further object of the present invention is to provide an ocular refracting power measuring system which can effectively eliminate any affection due to a turbidity in the crystalline lens and the cilia to improve the accuracy on measurement of ocular refracting power.

A further object of the rpesent invention is to provide a system which can embody an image processing means required on measurement of ocular refracting power.

A further object of the present invention is to provide an ocular refracting power measuring system which can rapidly perform the focusing.

A further object of the present invention is to provide a technique useful in improving the accuracy and operativeness on measurement of ocular refracting power.

A further object of the present invention is to provide an ocular refracting power measuring system which can detect any abnormal position of eye such as strabsmus, heterophoria and the like while at the same time measuring an ocular refracting power.

A further object of the present invention is to provide an ocular refracting power measuring system which can measure the shape of a cornea.

BRIEF DESCRIPTION OF THE DRAWINGS

FIG. 1A is a schematic view of the basic arrangement of an ocular refracting power measuring system according to the present invention.

FIG. 14A is a view showing the basic arrangement of another embodiment of an ocular refracting power measuring system according to the present invention.

FIG. 33A is a view showing the basic arrangement of a further embodiment of an ocular refracting power measuring system according to the present invention.

DETAILED DESCRIPTION OF PREFERRED EMBODIMENTS

Figure 1B:
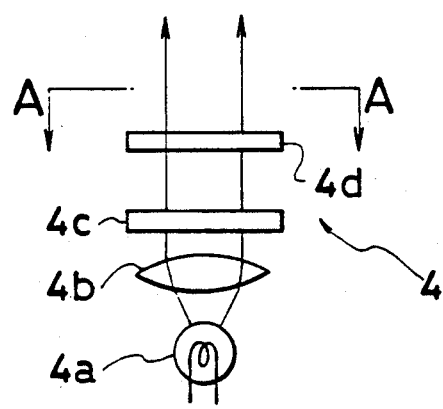
FIG. 1B is a view showing the construction of a light source.

Referring now to FIG. 1A, there is shown an ocular refracting power measuring system constructed according to the present invention, which comprises a projector system 1 for projecting the image of a light source onto the eyeground 7 of an eye to be tested 3 and a light receiver system 2 for receiving a light beam 10 reflected from the eyeground 7. These systems 1 and 2 are arranged opposite to the eye to be tested 3.

The projector system 1 comprises a light source 4 for emitting invisible rays such as infrared rays and a half-mirror 5 for reflecting a light beam 11 from the light source 4 toward the eye to be tested 3. The projector system 1 is adapted to project the light beam from the light source through the pupil 6 to image the light source 4 on the eyeground 7. In the projector system 1, the distance between the light source 4 and the eye to be tested 3 is set such that the light source 4 is focused and imaged on the eyeground 7 if the ocular refracting power of the eye to be tested 3 is a reference diopter (reference refracting power). A light source for emitting invisible rays such as infrared rays is exemplified in FIGS. 1B and 1C.

Figure 1C:
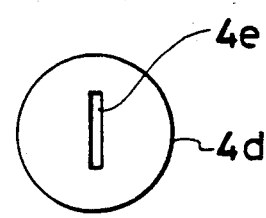
FIG. 1C is a view of the light source shown in FIG. 1B, as viewed in the direction of arrow A—A.

Referring to FIGS. 1B and 1C, the light source 4 comprises a light emitting element 4a, a condensing lens 4b located immediately adjacent to the light emitting element 4a, a visible light cutting filter 4c located immediately adjacent to the condensing lens 4b and for permitting the transmission of infrared rays and preventing the transmission of visible rays, and a stop plate 4d located immediately adjacent to the filter 4c and having a slitted opening 4e. The slitted opening 4e of the stop plate 4d extends in a direction perpendicular to the ridgeline of a edge-like light blocking member 12 which will be described later. The light blocking member 12 is adapted to block a portion of the slit-like light beam passed through the slit-like opening 4e.

If the visible light cutting filter 4c has a characteristic capable of transmitting near infrared rays, the stimulation of eyes to be tested can be reduced.

The light source 4 may be formed by a linear row of light emitting diodes which can emit infrared rays.

The opening of the stop plate 4d may be formed into any configuration other than the slit, for example, into a circular opening.

The light receiving system 2 comprises an objective lens 8 and a CCD camera including a light receiving element 9. The light beam 10 from the eyeground 7 is conducted onto the light receiving element 9 through the half-mirror 5.

The light receiving face 9a of the light receiving element 9 is disposed in a position conjugate with the pupil 6 of the eye to be tested 3 about the objective lens 8.

The edge-like light blocking member 12 is disposed at a position conjugate with the light source 4 about the half-mirror 5 such that the light beam 10 can be blocked by the light blocking member 12 only at one side with respect to the optical axis 0 of the objective lens 8.

The ocular refracting power measuring system further comprises a target watching system 13 which comprises a target to be watched 14, a lens 15 for projecting and imaging a light beam 18 from the target to be watched 14 onto the eyeground 7 of the eye to be tested, a mirror 16 for reflecting the light beam 18 passed through the lens 15 toward the optical axis in the projector system 1 and a dichroic mirror 17 disposed on the optical axis of the ocular refracting power measuring system such that the light beam 18 will be projected onto the eyeground 7 with the optical axis thereof being aligned with the optical axis of the ocular refracting power measuring system.

The target to be watched 14 may be take any suitable configuration, for example, such as plane geometric pattern, animals, stars in animated cartoons and others. Alternatively, the target to be watched itself may be formed by a doll or a stuffed toy.

The purpose of the dichroic mirror 17 is to reflect only visible rays from the target watching system 13 while permitting the transmission of invisible rays from the light source 4. This can improve the economy since the invisible rays can be utilized by the dichroic mirror 17 without increase of any waste rays.

If the power used therein is sufficient, however, the dichroic mirror 17 may be replaced by an suitable half-mirror.

The light source 4 and the light receiving element 9 are connected with an ocular refracting power judging circuit 19 which is adapted to calculate a diopter from a state under which the light receiving element 9 receives light with the result therefrom being supplied to a display 24.

The ocular refracting power judging circuit 19 will be described in more detail below.

The circuit 19 mainly comprises a drive circuit 20 for energizing the light source 4, a memory section 21 for storing the light receiving state in the light receiving element 9, a control section 22 for controlling the on-/off state of the light source 4 and a time when the memory section 21 stores the light receiving state of the light receiving element 9, and a processor section 23 for calculating a diopter from the information stored in the memory section 21 and applying the result thereof to the display 24.

In order to visually observe the state of a patient and his eye being tested on measurement, the display 24 is adapted to receive signals directly from the CCD camera (light receiving element 9) to display the images of the patient and his eye being tested.

The memory section 21 comprises a first memory 21a for storing image signals from the light receiving element 9 when the light source 4 is turned on, a second memory 21b for storing image signals from the light receiving element 9 when the light source 4 is turned off, a substractor 21c for subtracting the image signals of the second memory 21b from the image signals of the first memory 21c, and a third memory 21d for storing the resulting image signals from the subtractor 21c. The information of image stored in the third memory 21d is used to calculate the diopter.

The processor section 23 is adapted to calculate the diopter based on the light receiving state at the light receiving element 9 as described. Prior to further description of the processor section 23, the variations of the light receiving state due to various different diopter values will be described in the aforementioned arrangement of the optical systems.

Figure 2A:
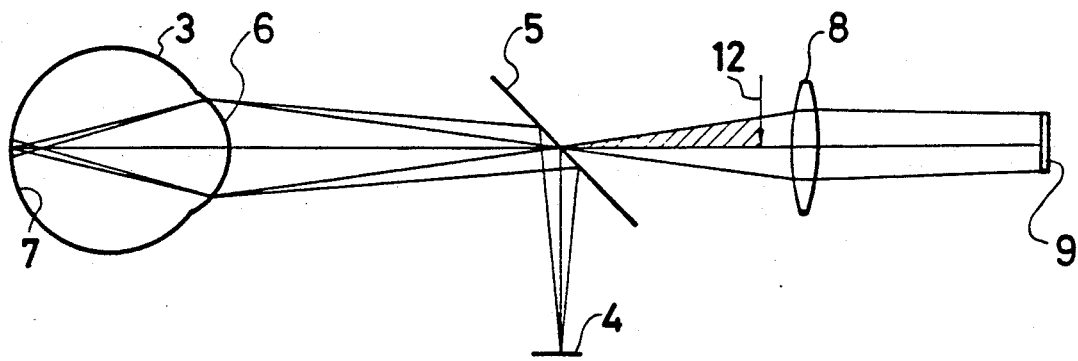
FIGS. 2A, 2B and 2C illustrate various different conditions of light beams due to various different diopters in eyes to be tested.

As shown in FIG. 2A, the image of the light source 4 is formed ahead of the eyeground 7 if the diopter value in the eye to be tested 3 is negative relative to the reference diopter value. This light beam is reflected by the illuminated eyeground 7 at a point on the optical axis to form a light beam 10. This light beam 10 is condensed ahead of the light blocking member 12, that is, on the side of the eye to be tested 3. As a result, the upper half of the light beam 10 projected onto the light receiving element 9 through the objective lens 8 will be blocked by the light blocking member 12, as shown by hatching in FIG. 2A.

Figure 2B:
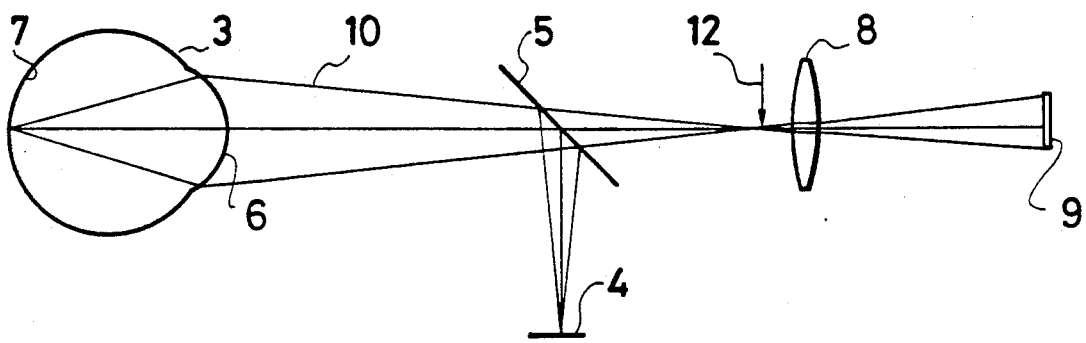

On the other hand, if the diopter value in the eye to be tested 3 is in the reference value, the light beam 10 will not be blocked by the light blocking member 12, as shown in FIG. 2B.

Figure 2C:
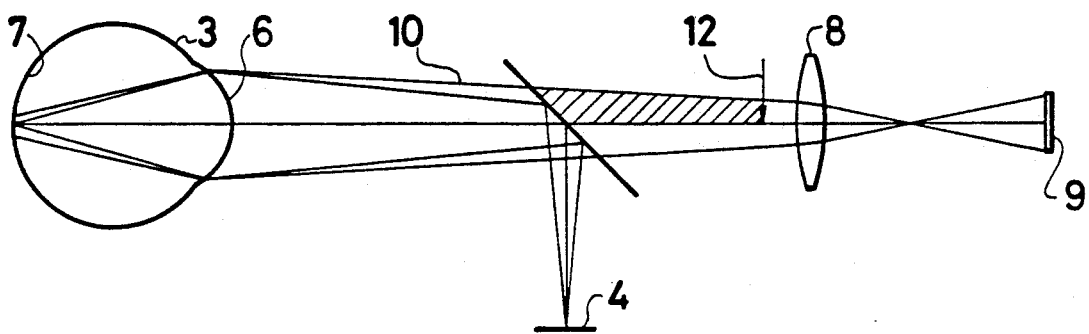

If the diopter value in the eye to be tested 3 is positive relative to the reference diopter value as shown in FIG. 2C, the light source 4 is imaged backward of the eyeground 7. The light beam 10 similarly reflected by the eyeground 7 is condensed backward of the light blocking member 12, that is, on the side of the light receiving element 9. As a result, the light beam 10 projected onto the light receiving element 9 will be blocked by the light blocking member 12 at a portion opposite to that of FIG. 2A (upper half in FIG. 2B).

In such a manner, the distribution of the light beam projected onto the light receiving surface 9a is varied depending on the level of the diopter value. Thus, a desired diopter value can be determined by measuring the distribution of light amount.

The light receiving element 9 serves to detect the distribution of the light beam formed on the light receiving surface 9a thereof with respect to the amount of light. The ocular refracting power judging circuit 19 is adapted to detect the distribution of light amount in the light beam formed on the light receiving surface 9a, based on signals from the light receiving element 9, thereby judging the refracting power of the eye to be tested whether it is positive or negative relative to the reference diopter value and calculating the absolute value thereof. The resultting value is then outputted to the display 24 wherein it is displayed.

Although the embodiment of the present invention has been described as to the use of half-mirror as beam separating means, it may be replaced by any other beam separating means such as a beam splitter, polarizing prism and so on.

The distribution of light amount in the light beam formed on the light receiving surface 9a will now be described in connection with FIGS. 3A through 3E.

For simplicity, it is assumed herein that the optical axis of the light source 4 is coincide with that of the light receiving system and that the light blocking member 12 is coincide with the objective lens 8. It is thus understood that the light source 4 is shown to be superposed on the objective lens 8 and the light blocking member 12 is omitted.

FIGS. 3A through 3E shows the case where the refracting power D of the eye to be tested is negative relative to the reference refracting power $D_0$. The following description will be performed by assuming that all the light beam reflected from the eyeground is projected onto the light receiving surface 9a through the objective lens 8.

Now assuming the distance between the light source 4 and the pupil 6 of the eye to be tested is set to be 1 and that the refracting power of the eye to be tested on which the image of the light source will be focused is at the reference refracting power $D_0$, the latter can be represented by:

$$D_0 = 1000/l \tag{1}$$

Figure 3A:
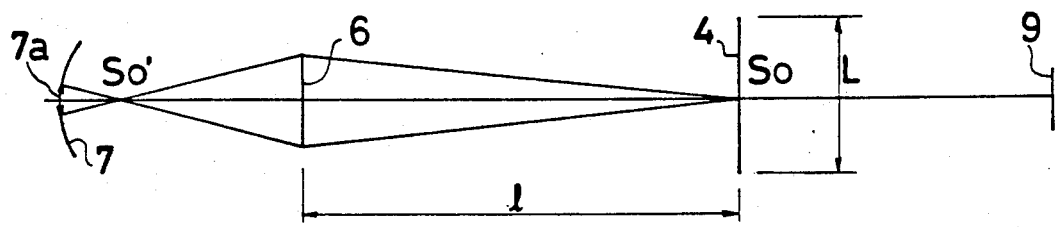
FIGS. 3A through 3E illustrate a light receiving element and the state of light beams reflected by the eyeground.

FIG. 3A shows a light beam projected from a point $S_0$ on the axis of a slit-like light source 4 which has its length L measured in the direction perpendicular to the optical axis, if the refracting power of the eye to be tested is D ($<D_0$). The image on the point $S_0$ is once re-imaged into $S_0'$. Such an image is projected onto the eyeground 7 as a faded image. As a difference between the ocular refracting power D and the reference refracting power $D_0$, that is, $D_0 - D$ increases, an imaging area 7a on which the image is to be projected will be widened.

Figure 3B:
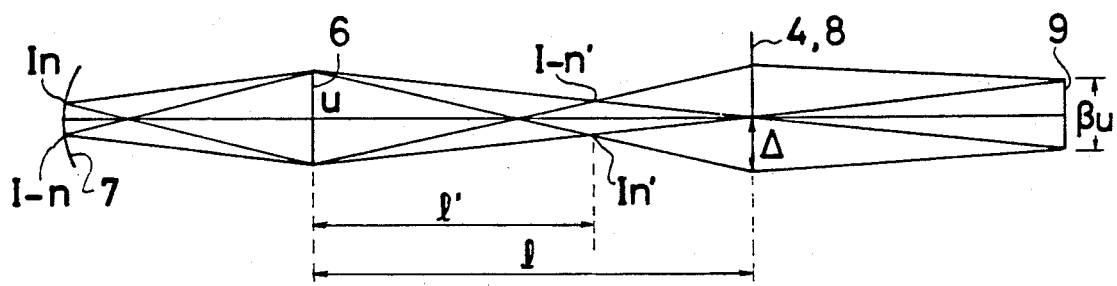

FIG. 3B shows the state of the light beam reflected by the eyeground 7 of the eye to be tested in the light receiving system 2.

Considering the light beam from a point $I_{-n}$ on the end of the projected area in the eyeground 7 as shown in FIG. 3B, the image $I_n'$ of this point will be imaged at a distance $l'$ from the pupil of the eye to be tested to form a light beam which in turn is projected, through the objective lens 8, onto the light receiving element 9 disposed at a position conjugate with the pupil 6 of the eye to be tested. The relationship between the distance $l'$ and the refracting power D of the eye to be tested is represented by:

$$D = -1000/l' \quad (2)$$

On the other hand, it can easily be understood from FIG. 3B that the increased width $\Delta$ of the light beam from one point on the eyeground at the edge is represented by:

$$\Delta = u \times (l - l')/l' \quad (3)$$

where u is the diamter of the pupil of the eye to be tested.

From the equations (1) and (2), the following equation can be obtained:

$$\begin{aligned}
\Delta &= u \times (l - l')/l' \\
&= u \left( \frac{\left(-\frac{1000}{D_0}\right) - \left(-\frac{1000}{D}\right)}{-\frac{1000}{D}} \right) \\
&= u(D/D_0 - 1) \\
&= u \times \Delta D/D_0
\end{aligned} \quad (4)$$

This means that the spread of the light beam on the light blocking member 12 increases as the difference between the refracting power D of the eye to be tested and the reference refracting power $D_O$.

The spreading of the light beam on the light receiving element 9 will be described. The light receiving element 9 is always disposed at a position conjugate with the pupil of the eye to be tested 3 about the objective lens 8, independently of the refracting power of the eye to be tested 3. Assuming that the diameter of the pupil 6 of the eye to be tested is u and the magnification of the objective lens 8 is $\beta$, the light beam will be projected onto the light receiving element 9 at an area which is represented by $\beta u$ and will not be affected by the refracting power of the eye to be tested.

The light beam from a point $I_n$ symmetrical to said point $I_{-n}$ about the optical axis is similarly imaged at the distance $l'$ from the pupil 6 of the eye to be tested to form an image $I_n'$ which in turn is projected onto the same area $\beta u$ on the light receiving element 9. If the light source 4 is a point-like configuration and the light blocking member does not exist, the distribution of light amount on the light receiving element 9 can be determined by integrating the light beams from various points $I_{-n}, \ldots I_0, \ldots I_n$ on the eyeground 7.

In order to consider the distribution of light amount on the light receiving element 9, it is assumed herein that a light beam enters the light receiving element 9 at an end position $P_n$ on the projected area thereof, that is, a coordinate $-\beta u/2$ about the optical axis. The light beam entering the light receiving element 9 at this position will be limited within the range of optical path shown by hatching A in FIG. 3C. Similarly, considering that a light beam enters the light receiving element 9 at a position $P_n$ symmetrical with said point $P_{-n}$ about the optical axis, the light beam will be limited within the range of optical path shown by hatching A' in FIG. 3C. It is understood from this that when the edge-like light blocking member 12 for blocking one of the light beams A' on the optical axis is disposed at a distance l from the pupil 6 of the eye to be tested (that is, a position conjugate with the light source 4), the light beam entering the light receiving element 9 at the position $P_{-n}$ will not be blocked by the light blocking member 12. The light beam is gradually blocked by the light blocking member 12 as the position shifts up from the position $P_{-n}$. At the central position $P_0$, the half of the light beam will be blocked by the light blocking member 12. At the position $P_n$, the entire light beam will be blocked by the light blocking member 12. Accordingly, the distribution of light amount has a constant gradient in which the amount of light decreases on the light receiving element 9 by the edge-like light blocking member 12 as the position shifts upward and finally becomes equal to zero at the point $P_n$.

Figure 3C:
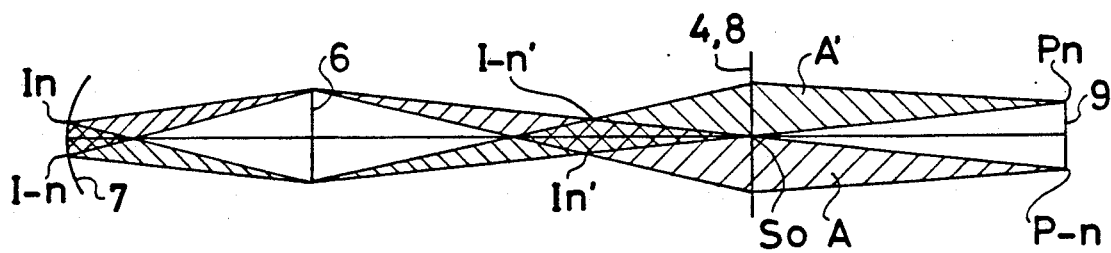
Figure 3D:
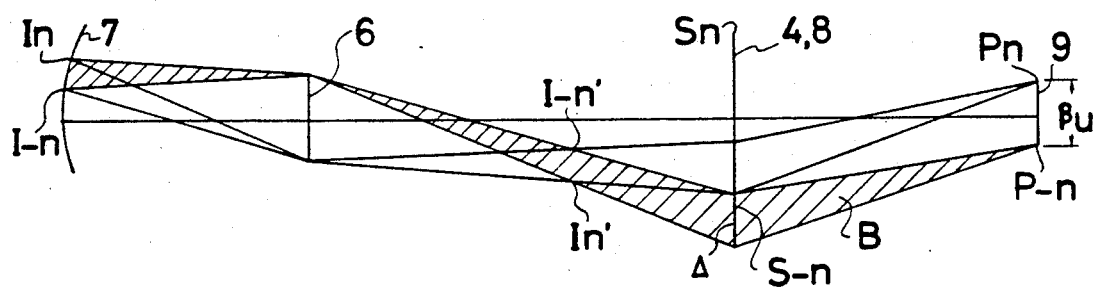

FIGS. 3A through 3C have shown only the light beam emitted from a point on the optical axis of the light source 4. However, FIG. 3D shows a light beam emitted from a point $S_{-n}$ on the end of the light source 4, that is, a point having a coordinate which is represented by $-L/2$ where L is the size of the light source. The light beam from this point $S_{-n}$ is projected onto an area on the eyeground 7 which is ranged between two points $I_{-n}$ and $I_n$, as shown in FIG. 3D. The light beams reflected from these points $I_{-n}$ and $I_n$ is imaged at a distance $l'$ spaced from the pupil 6 of the eye to be tested to form images $I_{-n}'$ and $I_n'$ which in turn are projected onto an area having a diameter $\beta u$ on the light receiving element 9. Among the light beams emitted from the end point $S_{-n}$ on the light source 4, a light beam entering an end position $P_{-n}$ in the projected area of the light receiving element 9 provides a light beam included within the hatched area B in FIG. 3D.

Figure 3E:
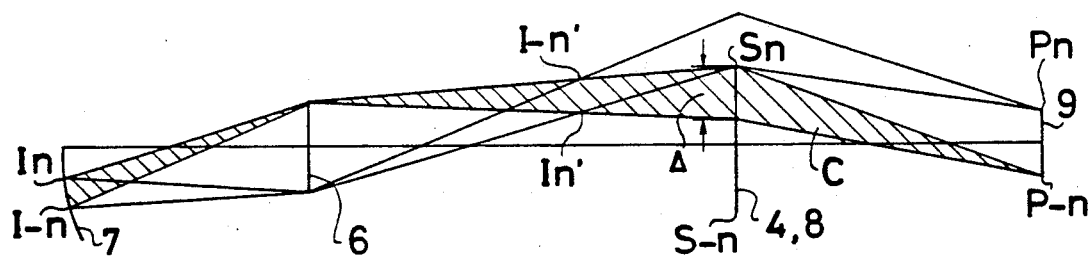

Also considering light beams emitted from a point $S_n$ symmetrical with said point $S_{-n}$ on the light source 4 and among them a light beam entering the point $S_{-n}$ on the light receiving element 9, there is provided a light beam included within the hatched area C in FIG. 3E. If it is considered that the light source 4 has a certain size, the amount of light on the light receiving element 9 at a point should be defined to be equal to the sum of those of the light beams from various points on the light source 4.

Figure 4A:
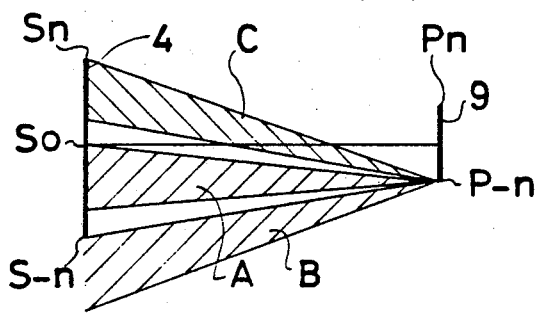
FIGS. 4A, 5A and 6A illustrate the state of light beams from various point on the light source to the light receiving element.

Based on such a definition, FIG. 4A shows a plurality of superposed light beams entering the point $P_{-n}$ on the light receiving element 9. Among light beams emitted from the position $S_{-n}$ on the light source, a light beam entering the position $P_{-n}$ will be represented by the hatched area B (see FIG. 3D). As the position on the light source shifts upward, the light beam relating thereto also shifts upward to provide a light beam included within the hatched area A at the position $S_0$ on the optical axis of the light source (see FIG. 3C). At the position $S_n$ on the light source, there is provided a light beam within the hatched area C (see FIG. 3E). It is thus understood that the amount of light on the light receiving element 9 at the point $P_{-n}$ is equal to the sum of these light beams.

Figure 4B:
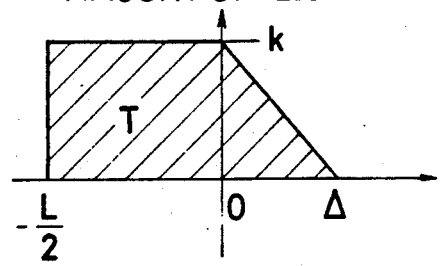
FIGS. 4B, 5B and 6B illustrate the variation of light amount in the respective light beams blocked by the light blocking member.

FIG. 4B diagrammatically shows the amount of light on the light receiving element 9 at the point $P_n$ when the light blocking member 12 is disposed at a distance l spaced away from the pupil 6 of the eye to be tested. FIG. 4B illustrates how the light beam is blocked by the light blocking member 12 as the position on the light source shifts. The horizontal axis of FIG. 4B represents the coordinate on the light source while the vertical axis thereof indicates the amount of light. Considering light beams emitted from the light source at various points thereon, light beams ranged between coordinate positions $-L/2$ (L is the size of the light source) and zero will not be blocked by the light blocking member 12 while light beams passed through the coordinate position 0 are gradually blocked by the light blocking member 12. At the position $\Delta$ (said spread in the light beam), the entire light beam will be blocked by the light blocking member. A combination of the light amount k of the unblocked light beams from the light source at the various points with that of the blocked light beams from the same is shown in FIG. 4B. It is noted herein that the hatched area T corresponds to the amount of light on the light receiving element at the point $P_{-n}$. Such an area T can be represented by:

$$T = \tfrac{1}{2}k(L+\Delta) \tag{5}$$

Figure 5A:
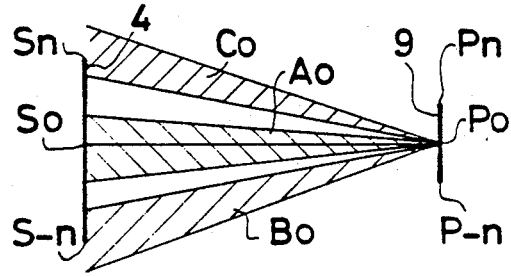
Figure 5B:
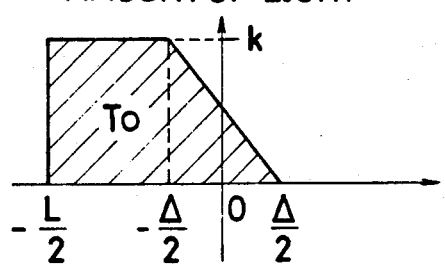

The other points on the light receiving element will be considered similarly. FIG. 5A shows light beams entering the central point $P_0$ on the light receiving element, in the same manner as that of FIG. 4A. Among light beams emitted from the light source at the point $S_{-n}$, a light beam entering the point $P_0$ is included within the hatched area $B_0$; among light beams emitted from the light source at the point $S_0$, a light beam entering the point $P_0$ is included within the hatched area $A_0$; and among light beams emitted from the light source at the point $S_n$, a light beam entering the point $P_0$ is included within the hatched area $C_0$. Thus, the amount of light on the light receiving element 9 at its center will correspond to the size of the hatched area $T_0$ shown in FIG. 5B. Namely, considering the light beams entering the central point of the light receiving element from various points on the light source, light beams ranged between the positions $-L/2$ and $-\Delta/2$ on the light source will not be blocked; light beams in any position beyond $-\Delta/2$ will be gradually blocked; and a light beam just in the position $\Delta/2$ will be completely blocked. In the same manner as mentioned previously, the entire area $T_0$ can be represented by:

$$T_0 = \tfrac{1}{2}kL \tag{6}$$

Figure 6A:
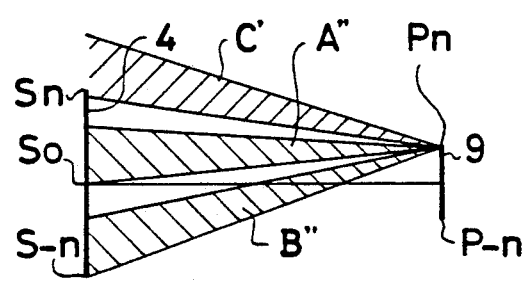
Figure 6B:
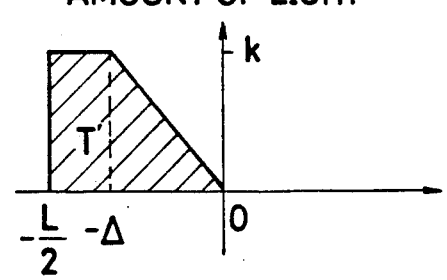

Similarly, the state and light amount of the light beams entering the light receiving element at the point $P_n$ are shown in FIGS. 6A and 6B. In FIG. 6A, among light beams emitted from the light source at the point $S_{-n}$, a light beam entering the point $P_n$ is shown to be within the hatched area B'; among light beams emitted from the light source at the central point $S_0$, a light beam entering the point $P_n$ is shown to be within the hatched area A''; and among light beams emitted from the light source at the point $S_{-n}$, a light beam entering the point $P_n$ is shown to be within the hatched area C''. At this time, considering the light beams entering the light receiving element at the point $P_n$ from various points on the light source as shown in FIG. 6B, the light beams ranged between positions $-L/2$ and $-\Delta$ will not be blocked; the light beams in any position beyond the position $-\Delta$ will be gradually blocked; and the entire light beam at the position 0 will be completely blocked. The value of this area can be calculated as follows:

$$T_0' = \tfrac{1}{2}k(L-\Delta) \tag{7}$$

Figure 7:
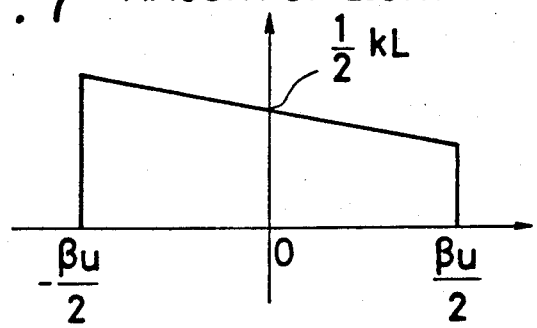
FIGS. 7, 8 and 9 illustrate the distribution of light amount corresponding to the diopters on the light receiving surface.

It will be apparent from these equations (5), (6) and (7) that the amount of light on the light receiving element 9 gradually decreases from the lower section to the upper section. The distribution of light amount on the light receiving element is shown to be linear in FIG. 7.

The above description is based on that the light beam emitted from the eyeground at a point has a spread $\Delta$ on the light blocking member 12 which is smaller than one-half of the size L of the light source.

Figure 10:
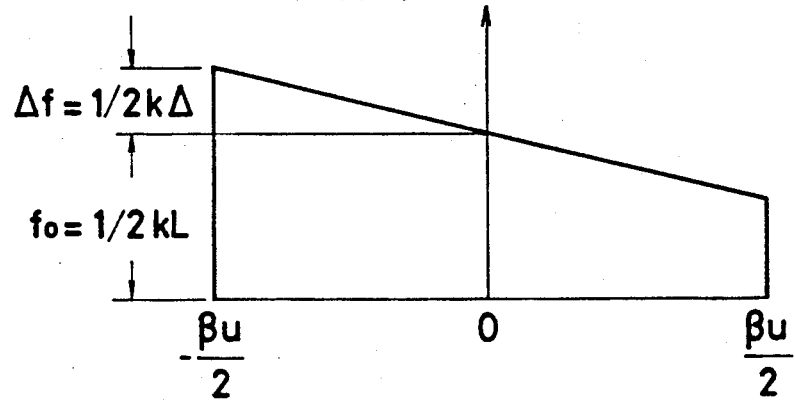
FIG. 10 illustrate the determination of diopter from the distribution of light amount.
Figure 11:
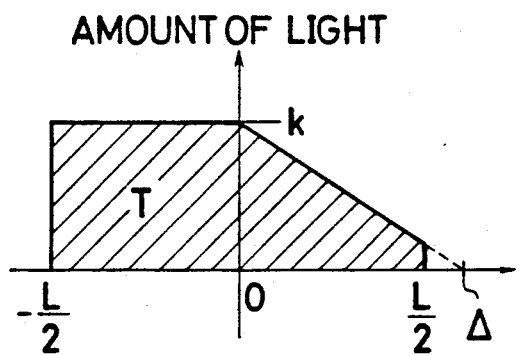
FIGS. 11, 12 and 13 illustrate the variation of light amount in the respective light beams when they are blocked by the light blocking member when the spread of each of the light beams on the light blocking member is larger than one-half of the size of the light source.
Figure 12:
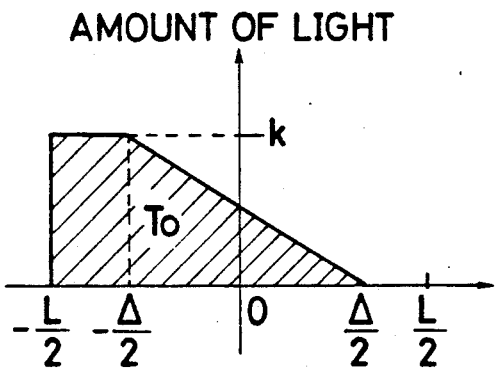
Figure 13:
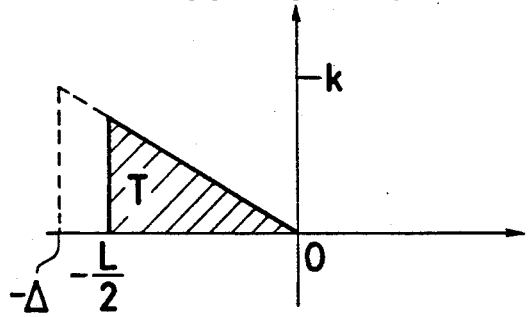

However, if $\Delta$ is larger than $L/2$, that is, if a difference D between the reference diopter $D_0$ and the diopter of an eye to be tested is equal to or larger than a predetermined level, there is no linear variation as shown in FIG. 10. This will now be described in connection with FIGS. 4 to 6. If $\Delta$ is larger than $L/2$ as mentioned above, FIGS. 4B, 5B and 6B can be redrawn into FIGS. 11, 12 and 13, respectively. This variation of the amount of light is not linear as in the FIG. 7.

Figure 8:
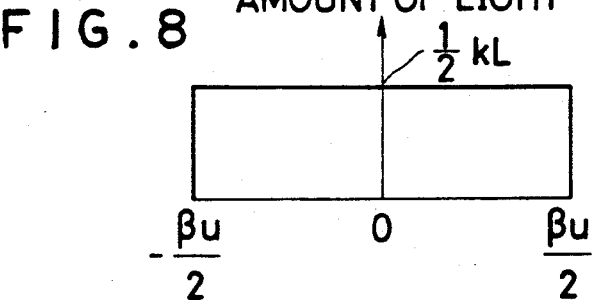
Figure 9:
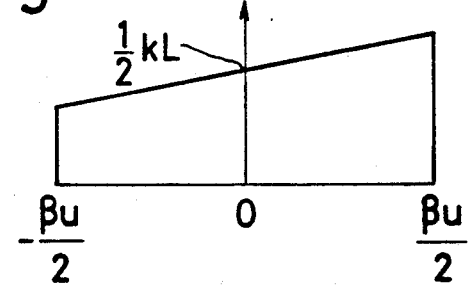

If the refracting power of the eye to be tested shown in FIG. 2B is equal to the reference level or if the refracting power of the eye to be tested shown in FIG. 2C is positive relative to the reference level, the distribution of light amount on the light receiving element 9 can be considered in the same manner as previously mentioned. When the refracting power of the eye to be tested is equal to the reference refracting power, the distribution of light amount will be uniform as shown in FIG. 8. When the refracting power of the eye to be tested is positive, the distribution is represented by a configuration opposite to those of FIG. 7.

In the above distribution of light amount, its gradient represents the diopter value (refracting power) and the direction of gradient indicates positive or negative diopter value. FIG. 10 will be referred to below.

When it is defined that the gradient in the distribution of light amount is $\Delta f/f_0$, the following equation can be provided:

$$\Delta f/f = (\tfrac{1}{2}k\Delta)/(\tfrac{1}{2}kL) = \Delta/L \tag{8}$$

The aforementioned spread $\Delta$ of the light beam, that is, obscurity can be obtained as follows:

From the equation (5), $$\Delta = u \times (l-l')/l' = u \times \Delta D/D_0 \tag{9}$$

Thus, from the equation (8), $$\Delta f/f_0 = u\Delta D/LD_0$$

Therefore, $$\Delta D = (LD_0/u)(\Delta f/f_0).$$

$$\Delta D = K(\Delta f/f_0), (K = LD_0/u) \quad (10)$$

This equation (10) indicates that the difference D between the reference diopter $D_0$ and the diopter of the eye to be tested is proportional to $(\Delta f/f_0)$. If the value $(\Delta f/f_0)$ is determined from the distribution of light amount, the deviation $\Delta$ of the diopter in the eye to be tested can be determined.

Therefore, the diopter D of the eye to be tested can be obtained from the following equation:

$$D = D_0 + \Delta D \quad (11)$$

The processor section 23 receives information relating such a light receiving condition as shown in FIG. 10 from the light receiving element 9 through the memory section 21 and calculates the deviation D in the diopter of the eye to be tested in accordance with the equation (10), based on the aforementioned information.

It is preferred that any external disturbance such as external rays is eliminated from the measurements to improve the accuracy of measurement.

The elimination of the affection of external rays may be accomplished by darkening a room in which the measuring system is mounted. However, the darkened room may strike terror into infants. It is preferred to make the measuring room bright.

The refracting power judging circuit 19 will be described in the case where it is used in a brightened room.

The control section 22 generates on/off control signals to the drive circuit 20 and the memory section 21.

On reception of a signal from the control section 22, the first memory 21a fetches and stores image signals from the light source 4 when it is turned on while the second memory 21b fetches and stores image signals from the light source 4 when it is turned off. The subtractor section 21c then subtracts the image signals stored in the second memory 21b from those stored in the first memory 21a. The results thereof are fetched by and stored in the third memory 21d and then processed by the processor section 23 to provide a diopter which in turn is displayed on the display device 24. The image signals in the first memory 21a when the light source 4 is turned on are initially superposed by signals from any external rays. When such image signals are subjected to the subtraction of the signals relating to the external rays, the third memory 21d will only store image signals having no affection due to the external rays. When these image signals are calculated to provide the diopter, therefore, measurements may be performed with increased accuracy without affection of any external rays.

It is a matter of course that a true deviation of diopter can be obtained also by varying the light source 4 in amount of light without on/off control of the light source 4.

In order to simplify the construction of the control circuit, the on/off control of the light source 4 may be performed successively depending on synchronization signals, rather than only on measurement.

The ocular refracting power measuring system has been described as to measurement of the diopter in one radial line.

However, the ocular refracting power measuring system of the present invention can be used to measure diopters in a plurality of radial lines to inspect the astigmatism.

The astigmatism is created due to different diopters in the radial lines and specified in its present state by measuring the spherical curvature S, degree of astigmatism C and angle of astigmatic axis A in that eye to be tested. The relationship between a diopter value D and the spherical curvature S, degree of astigmatism C and angle of astigmatic axis A can be represented by the following equation:

$$D_\theta = S + C \sin^2(\theta - A) \quad (12)$$

If diopters are determined with respect to three longitude lines $\theta_1$, $\theta_2$ and $\theta_3$, therefore, the spherical curvature S, degree of astigmatism C and angle of astigmatic axis A can be determined to specify the state of astigmatism.

In this connection, the target to be watched 14 is omitted in FIG. 14A.

As in FIGS. 1B and 1C, the light source 4 is adapted to emit a slit-like light beam. The arrangement is such that the slit-like light beam can be rotated about the optical axis in synchronism with the rotation of the light blocking member 12 which will be described later.

Figure 14B:
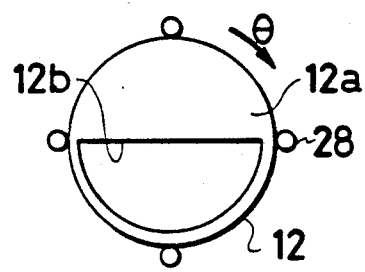
FIG. 14B is a view of the light blocking member shown in FIG. 14A, a viewed in the direction of arrow B—B.

As shown in FIG. 14B, the light blocking member 12 is of such a configuration that it is cut away to have a semi-circular opening remaining a semi-circular edge portion 12a. The ridgeline 12b of the edge portion 12a is disposed to align with the optical axis of the light receiving system 2. The light blocking member 12 is supported by rollers 27 for rotation about the optical axis in synchronism with the rotation of the light source 4.

Figure 14C:
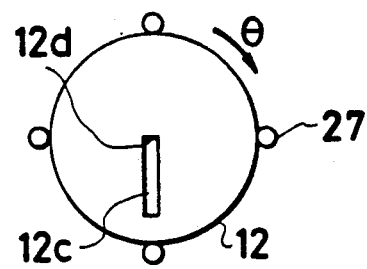
FIG. 14C is a view showing another form of the light blocking member.

Another example of the rotary light blocking member 12 is shown in FIG. 14C wherein it is formed with a slit 12c which is capable of blocking one-half of the slit-like light beam 10 with the boundary of the ridgeline 12d.

Since the astigmatism can be determined by measuring the diopters on the three radial lines $\theta_1$, $\theta_2$ and $\theta_3$, a diopter is first determined at one radial line $\theta_1 = 0°$. The light source 4 and the light blocking member 12 are then rotated to provide $\theta_2 = 60°$ and $\theta_3 = 120°$. At the respective rotated positions, diopters are measured.

In such a manner, the spherical curvature S, degree of astigmatism C and angle of astigmatic axis A can be obtained from the aforementioned equation (12) immediately after three rotated positions of the light blocking member 12 have been selected to measure diopters at the respective rotated positions.

Figure 15A:
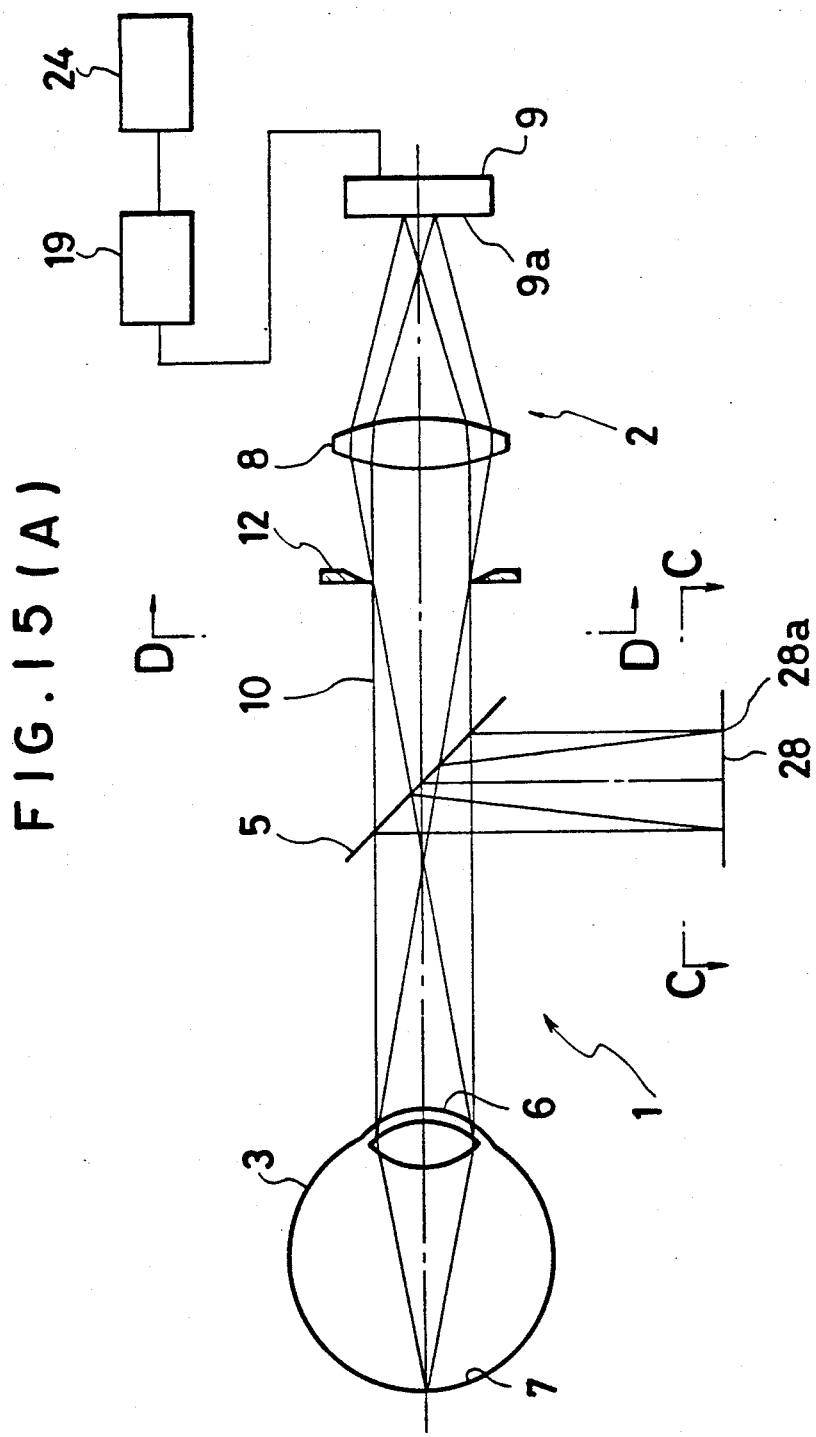
FIG. 15A is a view showing the basic arrangement of still another embodiment of an ocular refracting power measuring system according to the present invention.

FIG. 15A shows the second embodiment of the present invention in which diopters can be measured on a plurality of radial lines.

Figure 15B:
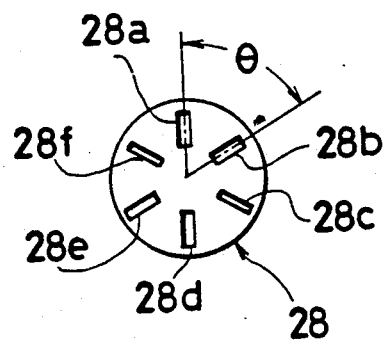
FIG. 15B is a view of the basic arrangement shown in FIG. 15A, as viewed in the direction of arrow C—C.

In the second embodiment, a light source 28 comprises a plurality of slit-like light source portions 28a, 28b ... 28f, as shown in FIG. 15B. These light source portions 28a through 28f can be selectively lighted on and are arranged within a plane perpendicular to the optical axis of the projecting system 1. Each of the light source portions is located on one the radial lines spaced apart from one another by an angular distance $\theta$ (e.g. 60°) about the optical axis. Each of the light source portions also is spaced radially apart from the optical axis by a predetermined radial distance.

Figure 15C:
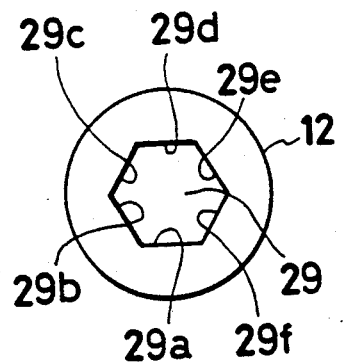
FIG. 15C is a view of the basic arrangement shown in FIG. 15A, as viewed in the direction of arrow D—D.

As shown in FIG. 15C, the light blocking member 12 is formed with a hexagonal opening 29, the center of which is positioned to align with the optical axis of the light receiving system 2. The hexagonal opening 29 has edge-like ridgelines 29a, 29b . . . 29f, each of which is positioned at a position corresponding to each of the light source portions 28a, 28b . . . 28f and perpendicular to a radial line to which that light source portion belongs. With the reference diopter value, each of the light source portions is adapted to be formed on the corresponding ridgeline.

In the second embodiment, if light sources on at least three different radial lines (except a light source on a radial line diametrically opposed to each of said different radial lines) as shown by 28a, 28b and 28c in FIG. 15B are selectively lighted on one at a time to perform such measurements as described hereinbefore, diopters on the three radial lines can be determined such that the spherical curvature S, degree of astigmatism C and angle of astigmatic axis A can be obtained immediately from said equation (12).

Figure 16A:
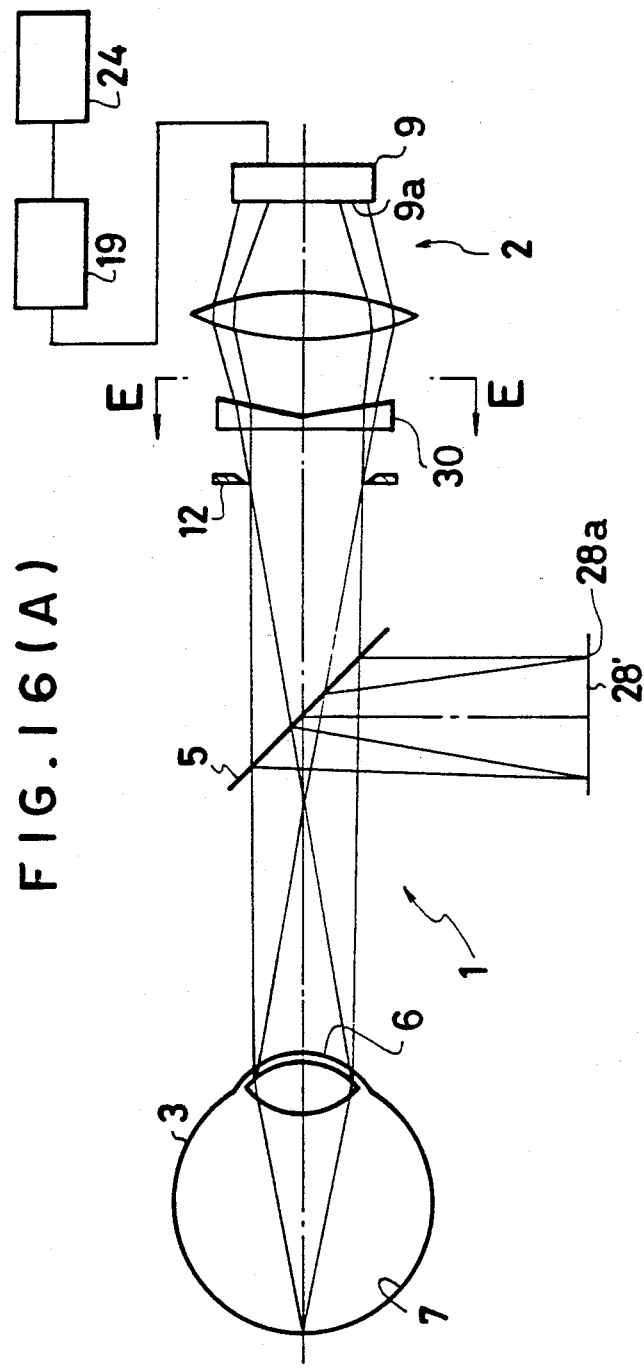
FIG. 16A is a view showing the basic arrangement of a further embodiment of an ocular refracting power measuring system according to the present invention.
Figure 16B:
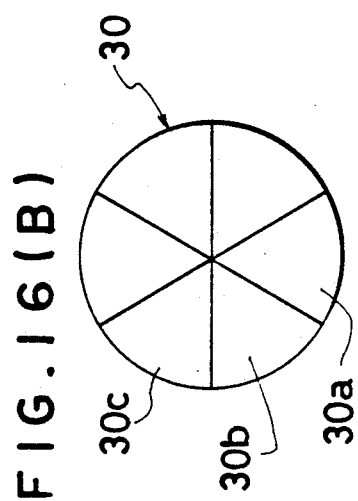
FIG. 16B is a view of the basic arrangement shown in FIG. 16A, as viewed in the direction of arrow E—E.

FIG. 16A shows the third embodiment of an ocular refracting power measuring system according to the present invention, which comprises a light source 28' substantially similar in construction to that of the second embodiment and the same light blocking member 12 as that of the second embodiment. The light source portions 28a, 28b, 28c . . . 28f of the light source 28' will not selectively be turned on and off unlike those of the second embodiment. The ocular refracting power measuring system also comprises an objective lens 8 and light beam diverging means such as a deflection angle prism 30 disposed between the light blocking member 12 and the objective lens 8 and adapted to deflect light beams from the light source portions 28a, 28b, 28c 28d . . . 28f away from the optical axis of the light receiving system 2. The deflection angle prism 30 comprises a plurality of prism pieces 30a, 30b, 30c . . . 30f respectively corresponding to the light source portions 28a, 28b, 28c . . . 28f, which are arranged radially about the optical axis.

Since the light beams from the respective light source portions 28a, 28b, 28c . . . 28f are projected onto the light receiving face 9a at different locations, the aforementioned measurement may be made on the light receiving face 9a at each of the different locations to obtain a diopter. In such a manner, diopters on a plurality of radial lines can be determined simultaneously and the spherical curvature S, degree of astigmatism C and angle of astigmatic axis A will also be obtained.

Figure 17:
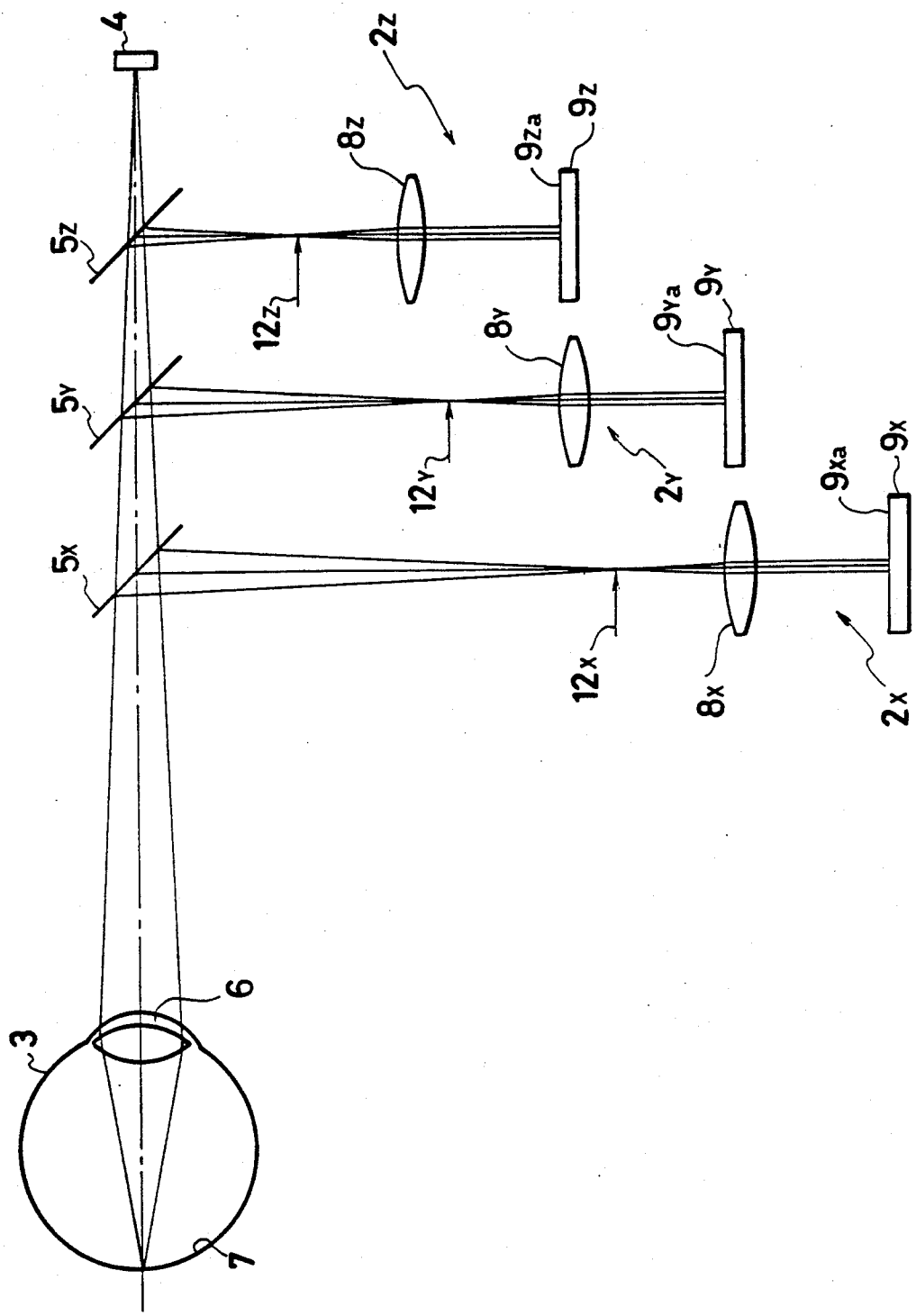
FIG. 17 is a view showing the basic arrangement of a further embodiment of an ocular refracting power measuring system according to the present invention.

FIG. 17 shows the fourth embodiment of an ocular refracting power measuring system according to the present invention, which comprises a light source 4 having a circular light emitting portion and disposed opposed to an eye to be tested 3 and light receiving systems 2x, 2y and 2z each having an optical axis perpendicular to the optical axis of the eye to be tested 3 and disposed spaced away from one another in a plane including the optical axis of the eye to be tested 3. Halfmirrors 5x, 5y and 5z are arranged on the optical axis of the eye to be tested 3. Each of the half-mirrors 5x, 5y and 5z is adapted to split and deflect a light beam from the eyeground 7 toward the corresponding light receiving system 2x, 2y or 2z.

Each of the light receiving systems 2x, 2y and 2z includes a light receiving element 9x, 9y or 9z having its light receiving face 9xa, 9ya or 9za which is located at a position conjugate with the pupil 6 of the eye to be tested 3 about the corresponding objective lens 8x, 8y or 8z, as in the previous embodiments. A light blocking member 12x, 12y or 12z is located within the optical path of the corresponding light receiving system 2x, 2y or 2z at the same position as in the previous embodiments. Each of the light blocking members 12x, 12y and 12z has the same slitted opening as shown in FIG. 14C. The light blocking member 12y is positioned at an angular position spaced away from the light blocking member 12x by 60° while the light blocking member 12z is positioned at an angular position further spaced away from the light blocking member 12y by 60°.

In such an arrangement, diopters simultaneously obtained when the light receiving element 9x, 9y and 9z receive light beams will relate to three radial lines.

In the third embodiment of FIG. 17, the diopters on the three radial lines may be similarly determined even though the light receiving systems 2x, 2y and 2z have the completely same structure and the directions of the light beams split and reflected by the respective halfmirrors are assigned to 0°, 60° and 120° to arrange the light receiving systems 2x, 2y and 2z radially relative to the optical axis of the eye to be tested.

Measurement of astigmatism can be performed by determining at least three ocular refracting powers. Alternatively, ocular refracting powers relating to two radial lines may be measured to determine the state of astigmatism.

Measurement of ocular refracting powers on two radial lines may be accomplished by means of such a mechanical arrangement as shown in FIGS. 14A, 14B and 14C. In such a case, the light source 4 and the light blocking member 12 may be rotated for determining ocular refracting powers on two radial lines.

Astigmatism is due to the fact that an eye to be tested is not perfectly spherical. If an eye to be tested is of a perfectly spherical configuration without astigmatism, the distribution of light amount would be constant in the direction parallel to the ridgeline of the edge. If the distribution of light amount in the same direction is changed from one to another, this represents the presence of any astigmatism.

Figure 18:
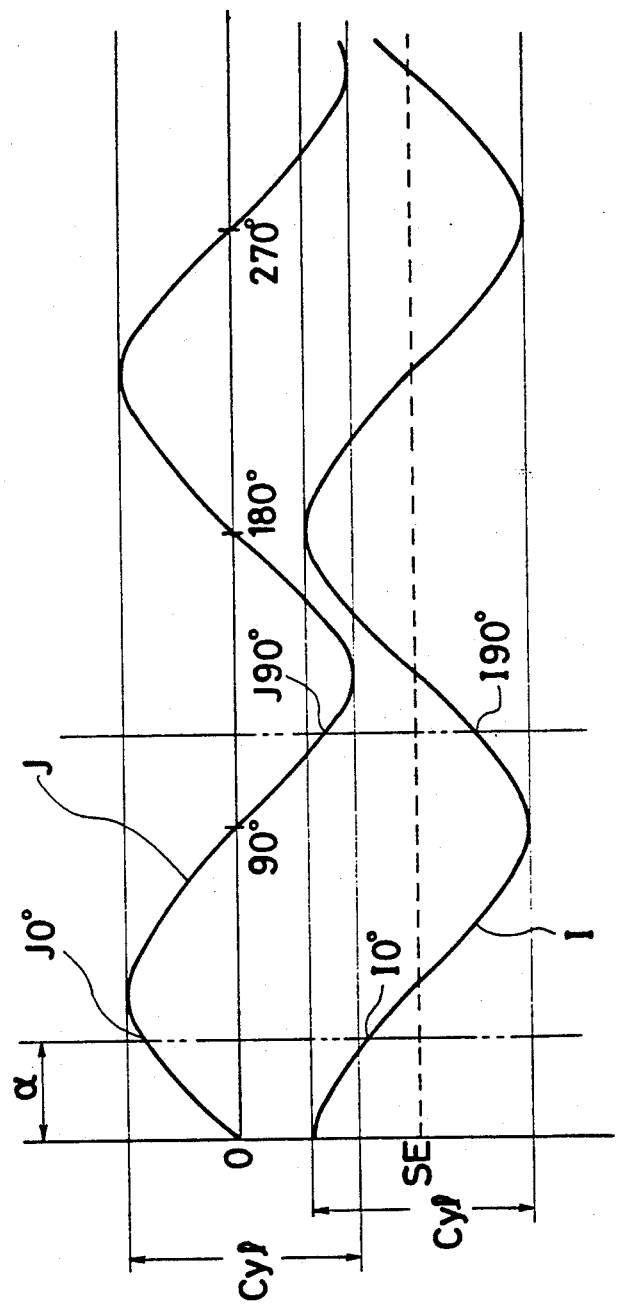
FIG. 18 illustrates the relationship between coefficients relating to the amount of light on the light receiving surface and angles of meridian.

Assuming that a direction perpendicular to the ridgeline of the edge is x-direction and a direction parallel to the same ridgeline is y-direction, the distribution of light amount L on the light receiving element in the CCD camera can be generally represented by:

$$L(x,y) = I \cdot x + J \cdot y + K \tag{13}$$

where I and J are functions of SE, Cyl and Axs where SE is the spherical curvature of the eye to be tested, Cyl is the astigmatic degree and Axs is the astigmatic axis angle. If the values of I and J are plotted and simulated on the horizontal axis as the astigmatic axis, furthermore, it has been found that these values draws two sine curves shifted in phase from each other by 90°, as shown in FIG. 18. In other words, the value of J becomes zero if the astigmatic axis is parallel or perpendicular to the ridgeline of the edge. This means that the amount of light becomes constant in the direction parallel to the ridgeline of the edge and then varies along the sine curve. This sine curve has an amplitude corresponding to the astigmatic degree Cyl.

On the other hand, the values of I draws a sine curve located out of phase to the sine curve of J by 90° and moved parallel to the sine curve of J by an amount equal to the difference between the spherical curvature SE and the reference diopter $D_0$ in the eye to be tested, $(SE - D_0)$.

When a plane passing through the center of the pupil of an eye to be tested is horizontal (i.e. 0°) and a plane including a radial line to be estimated (X-direction)

forms an angle equal to $\theta$ with the horizontal plane, I and J are represented by:

$$I(\theta, SE, Cyl, Axs) = (SE - D_0 + Cyl/2X \cos 2(\theta - Axs))Xk, \text{ and}$$

$$J(\theta, Cyl, Axs) = (Cyl/2X \sin 2(\theta - Axs))Xk \quad (14)$$

where k is a coefficient determined by the diameter of the pupil, the reflectivity of the eyeground and the shape of the light source, and $D_0$ is a reference diopter value.

As be apparent from the above equations (14), the distribution of light amount L may be measured by the equation (13) on the respective one of two radial lines ($O_2 \neq \theta_1 + n\pi$) to determine the values of SE, Cyl and Axs from the resulting gradients $I_1$, $I_2$ and $J_1$, $J_2$.

If the angles $\theta$ and $\theta_2$ of the radial lines to be estimated are assumed to be in orthogonal directions, that is, 0° and 90°, there is no doubt that the calculation may be facilitated.

It is also possible to estimate more than two radial lines and to use any suitable calculating means such as averaging, approximation and the like to improve the accuracy of measurement.

Values of SE, Cyl and Axs when values of O are equal to 0° and 90° can be determined as follows:

$$I_{0°} = (SE - D_0 + Cyl/2 \cdot \cos(2 \cdot Axs))xk;$$

$$J_{0°} = (-Cyl/2 \cdot \sin(2 \cdot Axs))xk;$$

$$I_{90°} = (SE - D_0 - Cyl/2 \cdot \cos(2 \cdot Axs))xk; \text{ and}$$

$$J_{90°} = (+Cyl/2 \cdot \sin(2 \cdot Axs))xk \quad (15)$$

Therefore, $$SE = \tfrac{1}{2}k(I_{0°} + I_{90°}) + D_0;$$

$$Cyl = 1/k(I_{0°} - I_{90°})^2 + (-2J_{0°})^2; \text{ and}$$

$$Axs = \tfrac{1}{2} \cdot \tan^{-1}(-2J_{0°}/I_{0°} - I_{90°}) \quad (16).$$

Since $(J_{0°} - J_{90°})$ becomes respectively equal to $-2J_{0°}$ and $2j_{90°}$ when the values of $\theta$ are equal to 0° and 90°, the values of SE, Cyl and Axs can be determined from the equations (16) only by the use of three values, that is, one of the values of $J_{0°}$ and $J_{90°}$ and two values of $I_{0°}$ and $I_{90°}$.

This will be concretely described with reference to FIGS. 14A and 14B.

As described hereinbefore, the measurement of astigmatism can be performed by measuring two radial lines and the distribution of light amount in a direction perpendicular to each of the radial lines.

Light beam emitted from the light source 4 and reflected from the eyeground is blocked at its upper half by the edge portion 12a on the light blocking member 16. The light beam is then projected onto the light receiving face 9a through the objective lens 8 to form an image. The lightness in such an image gradually increases or decreases in a direction perpendicular to the ridgeline of the edge portion (X-direction), depending on the magnitude of the ocular refracting power of an eye to be tested relative to the reference diopter.

Signals from the light receiving element 9 contains lightness signals at one of points along the direction perpendicular to the ridgeline of the edge (X-direction). These lightness signals are fetched and used in the ocular refracting power judging circuit 19 to calculate the distribution of light amount. At this time, the distribution of light amount has a gradient which is $I_0$ in the equation (13).

Lightness signals on the light receiving element 9 at the respective points along a direction passing through the center of the image and extending parallel to the ridgeline of the edge (Y-direction) are fetched and used similarly in the ocular refracting power judging circuit 19 to calculate the distribution of light amount. At this time, a gradient in the distribution of light amount is $J_0$ in said equation (13).

If the X-direction forms an angle of $\alpha$ with the astigmatic axis (Axs), these gradients are shown on curves I and J of FIG. 18 at points $I_{0°}$ and $J_{0°}$, respectively.

Gradient $I_{0°}$ in the distribution of light amount along the X-axis is influenced by the degree of astigmatism corresponding to $(SE - I_{0°})$.

Gradient $J_{0°}$ in the distribution of light amount along the Y-axis is influenced only by the astigmatism and becomes smaller than Cyl/2.

Next, the light source 4 and the light blocking member 12 are rotated through 90° and the ocular refracting power judging circuit 19 calculates the distribution of light amount in each of the X- and Y-directions and their gradients $I_{90°}$ and $J_{90°}$. These gradients are shown on the curves I and J in FIG. 18.

The four points $(I_{0°}, I_{90°})$ and $(J_{0°}, J_{90°})$ are placed on a sine curve having its amplitude Cyl, and the curves I and J are shifted in phase from each other by 90°. Thus, the curves I and J are determined and further the values of SE, Cyl and Axs are determined.

The ocular refracting power judging circuit 19 calculates the values of said four points $I_{0°}$, $I_{90°}$ $J_{0°}$ and $J_{90°}$ and the spherical curvature SE, astigmatism degree Cyl and astigmatic axis Axs, all of which in turn are displayed on the display 24.

There are various types of arrangements for measuring the distribution of light amount in each of the X- and Y-directions on the edge at different positions. For example, slit-like light sources as shown by 28a, 28b and 28c in FIG. 15B may be placed on four radial lines extending in two directions perpendicular to each other. Alternatively, an opening as shown by 29 in FIG. 15C is configured into a square.

As described above, a diopter of an eye to be tested can be determined from the distribution of a light beam reflected by the eyeground. Astigmatism can also be measured by measuring diopters on a plurality of radial lines. However, the distribution of light amount thus measured is not considered with respect to any affection due to turbidity in the crystalline lens, the cilia or others.

Figure 19:
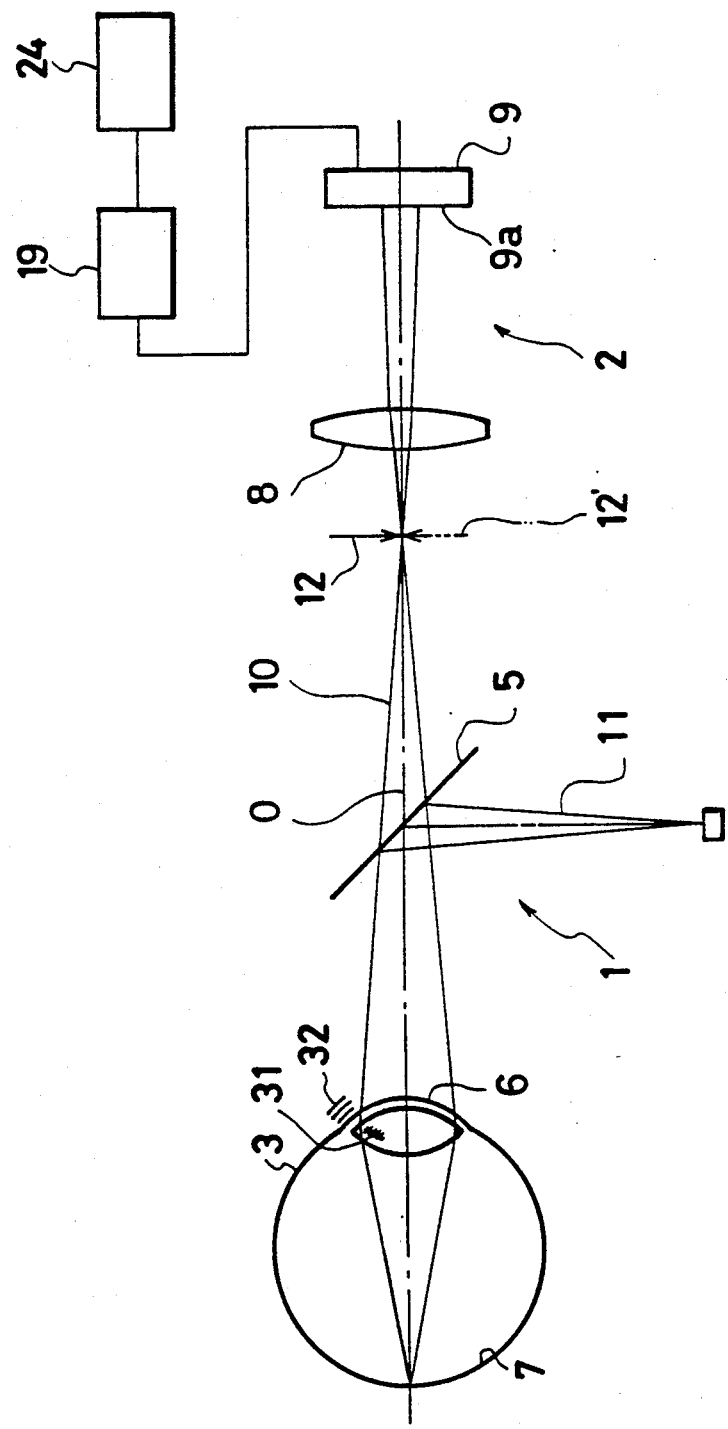
FIG. 19 is a view showing the basic arrangement of a further embodiment of an ocular refracting power measuring system according to the present invention.
Figure 20:
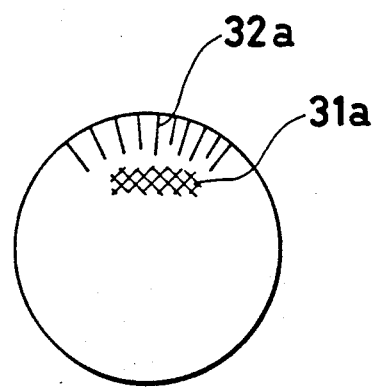
FIG. 20 is a view illustrating the image of a pupil as be observed.

The actual measurement is influenced by a turbidity 31 in the crystalline lens and the cilia 32 of an eye to be tested as shown in FIG. 19. The image of the pupil formed on the light receiving face 9a contains a shade or image 31a of the turbidity 31 in the crystalline lens (reduction of light amount) and images 32a of the cilia (see FIG. 20). These images 31a and 32a influence the distribution of light amount shown in FIG. 10, which will have recessed portions as shown by 31a and 32a in FIG. 21. If gradient is determined without elimination of the influence due to the undesirable images 31a and 32a, thus, the gradient will be larger than the actual gradient as shown by two-dot chain line in FIG. 21. This is because the undesirable images 31a and 32a are present behind the light blocking member 12 to provide the recessed light amount portions in such an area that the amount of light has been already reduced.

If the half of the light beam opposite to that blocked by the light blocking member 12 is blocked by another light blocking member 12', the recessed light amount portions appear in such an area that the amount of light is increased in the distribution. Under such a condition, the distribution of light amount is average to provide a gradient shown by two-dot line in FIG. 22.

Figure 21:
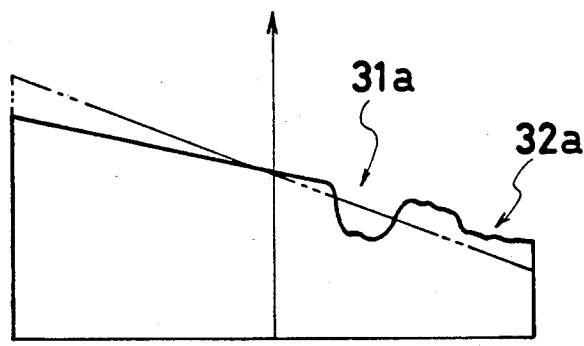
FIGS. 21 and 22 are views illustrating affections of the turbitity of crystalline lens and the cilia against the distribution of light.
Figure 22:
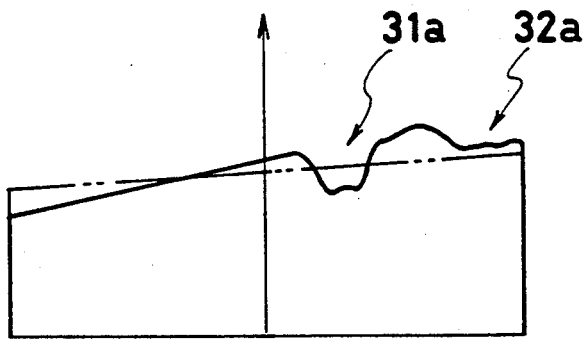

The increase of gradient shown by two-dot chain line in FIG. 21 and the decrease of gradient shown by two-dot chain line in FIG. 22 are both due to the same cause, that is, undesirable images 31a and 32a. If the gradient of FIG. 21 is added to the gradient of FIG. 22 and the resulting sum is then averaged, therefore, there would be obtained a true gradient without any affection of cilia, that is, a gradient due to the ocular refracting power.

Such an averaging operation may be accomplished by the embodiment shown in FIGS. 14A and 14B.

Under such a state as shown in FIG. 14B, the distribution of light amount is first measured through the edge portion 12a. The light blocking member 12 is rotated through 180° by any suitable means. The measurement of light is again performed to provide measurements similar to those obtained when the light beam is blocked one half at a time as described.

If it is desired to measure the astigmatism, measurements are made at the respective angular positions of the light blocking member 12, that is, a reference 0° position, a position rotated from the reference position by 180°, a position rotated from the reference position by 60°, a position rotated from the 60° position by 180°, a position rotated from the reference position by 120° and a position rotated from the 120° position by 180°. By averaging measurements on the same radial line, the astigmatism can be measured without any affection due to the cilia.

If in the embodiment of FIGS. 15A, 15B and 15C at least three sets of light source portions on three different radial lines (for example, 28a, 28d; 28b, 28e; 28c, 28f) are selectively lighted on one set at a time to make similar measurements, a diopter relating to three radial lines can be determined without affection of the turbitity in the crystalline lens and the cilia.

The calculation of diopter according to the present invention will be described more concretely below.

The aforementioned distribution of light amount is diagrammatically described. However, the actual distribution of light amount contains variations of light amount relative to various parts of an eye to be tested as shown in FIG. 23A (the distribution of light amount shown in FIG. 23B is based on the reference diopter), that is, a peak amount of light $\rho$ at a bright point 33 due to the reflection from the cornea, a reduction of light amount $\sigma$ at the part of the iris out of the pupil 6 and others.

Figure 23:
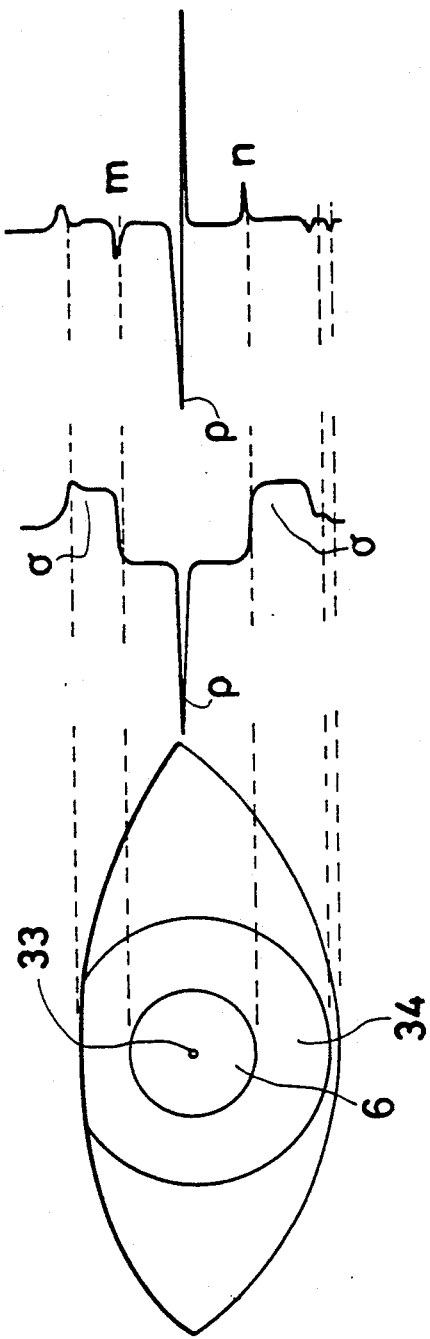
FIG. 23A is a view illustrating an eye to be tested.
FIG. 23B is a graph illustrating the distribution of light in the eye to be tested.
FIG. 23C is a graph illustrating the variations of the distribution of light.

According to the present invention, boundary points m and n on the pupil 6 are determined from said distribution of light amount and more concretely from the rate of variation in the amount of light shown in FIG. 23C and then used to determine the diameter u of the pupil.

If it is wanted to determine any deviation D between the diopters from the aforementioned distribution of light amount, any affection due to the bright point is not considered. However, any bright point actually influences measurements. It is thus preferred to eliminate the influence due to the bright point on measurement.

The following description will include the elimination of the influence due to the bright point.

Figure 24:
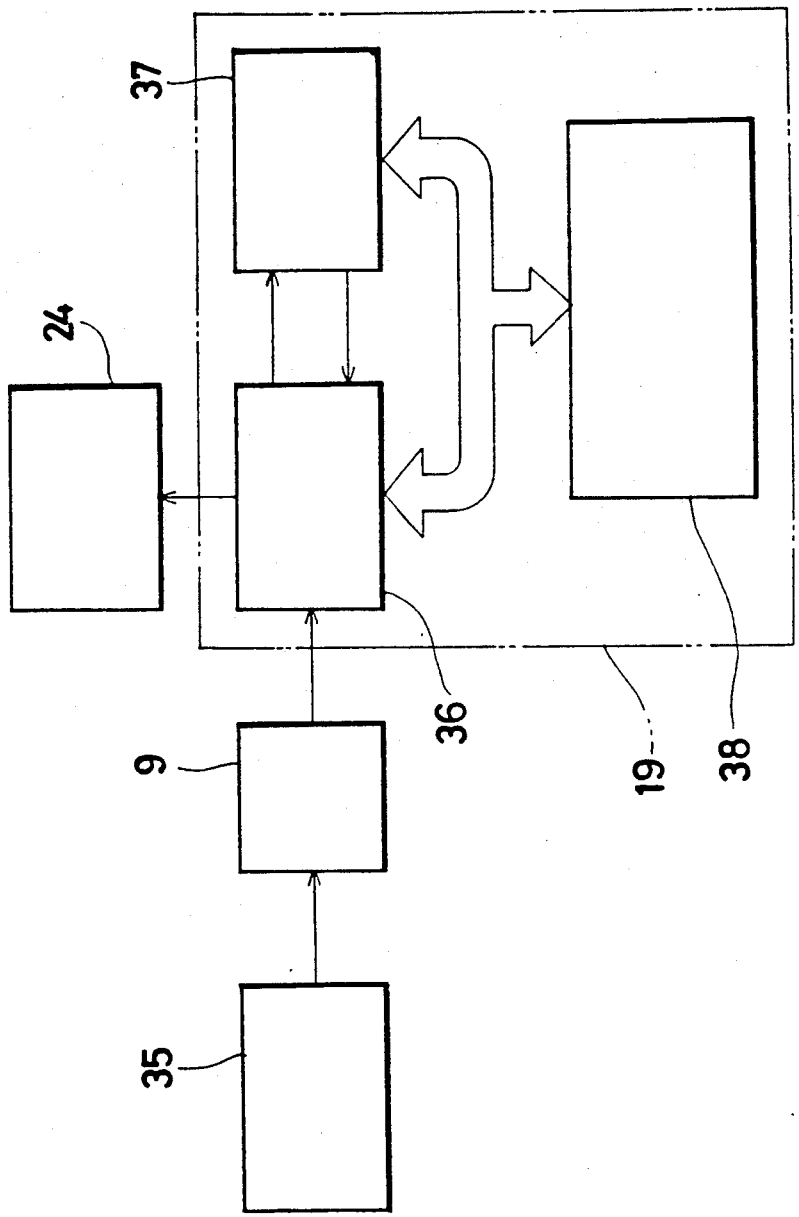
FIG. 24 is a block diagram of a further embodiment of an ocular refracting power measuring system according to the present invention.
Figure 25:
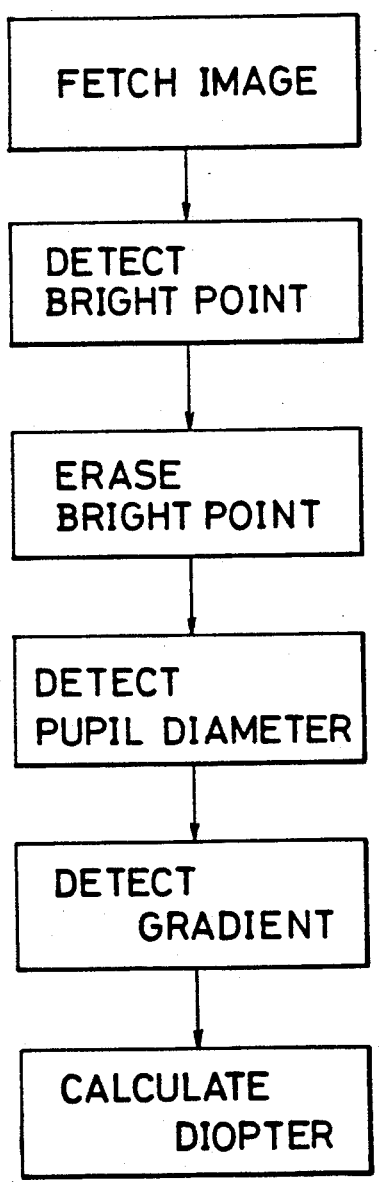
FIG. 25 is a flowchart illustrating the system shown in FIG. 24.

FIG. 24 is a block diagram of one embodiment of the present invention. In FIG. 24, reference numeral 35 denotes an optical system in said ocular refracting power measuring apparatus; 9 a light receiving element; 19 an ocular refracting power judging section; 24 a display; 36 a frame memory for storing image signals from the light receiving element 9 and the results from a processor 37; and 18 a controller for performing the synchronization and sequence commands with respect to the frame memory and processor 36 and 37.

This embodiment will now be described with reference to FIGS. 25 through 29.

Figure 26A:
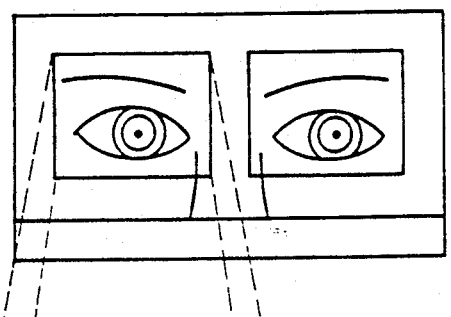
FIG. 26A is a view showing a scene observed by the ocular refracting power measuring system.
Figure 26B:
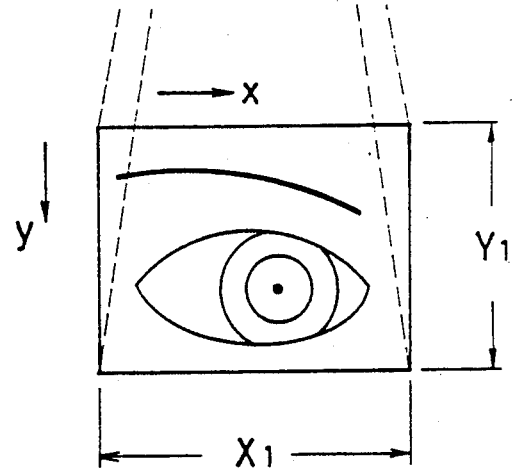
FIG. 26B is a view showing, in an enlarged scale, one of the eyes to be tested.

The face of a patient including his eyes is picked up by the light receiving element 9 to form an image which in turn is stored in the frame memory 36. Such an image is such formed that both the eyes are respectively included within preselected areas, for example, with the right eye being included within an area represented by ($X_1$; $Y_1$). FIG. 26B shows such an area ($X_1$; $Y_1$), in an enlarged scale.

Next, the maximum amount of light, that is, the maximum potential at the area ($X_1$; $Y_1$) in the frame memory 36 is determined.

If the maximum potential point at the area ($X_1$; $Y_1$) is determined, this is a bright point 33 which is formed by the mirror reflection in the cornea of the eye to be tested. Thus, the position of said bright point 33 can be determined from the bit location of the bright point within the frame memory 36.

Figure 27A:
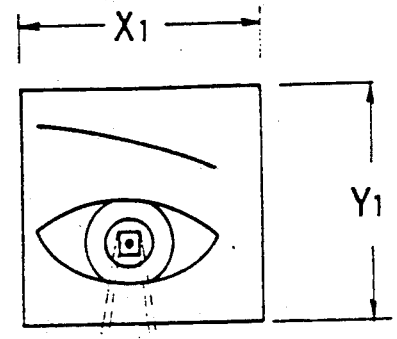
FIG. 27A is a view similar to FIG. 26B, showing the eye to be tested.
Figure 27B:
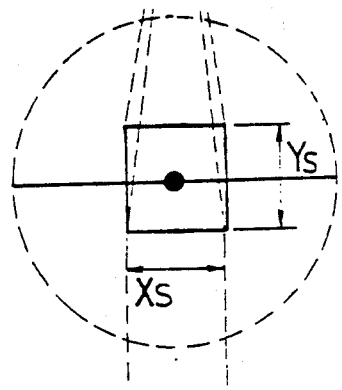
FIG. 27B is a view showing a range in which a bright point is included.
Figure 27C:
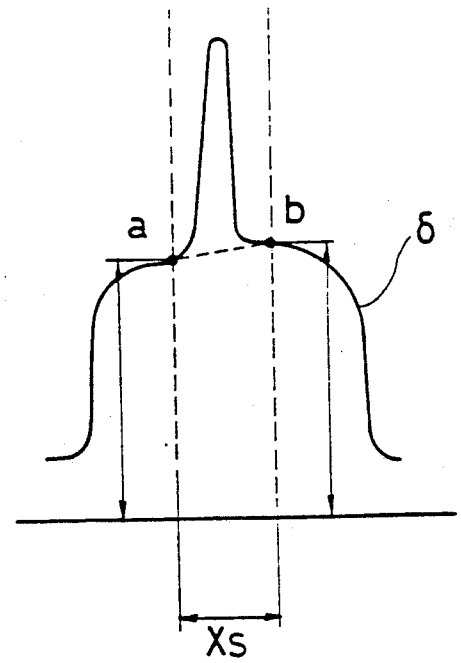
FIG. 27C is a graph showing the distribution of light on a scan line which runs parallel to an edge and which passes through the bright point.

After the bright point 33 has been determined, there is then set a detection area ($X_s$; $Y_s$) near the center of the bright point, as shown in FIG. 27B. A scan line extending in a direction X parallel to the edge is then used to determine the amount of light at each of points a and b which intersect the boundary line in the detection area ($X_s$; $Y_s$). These points a and b are then connected with each other by a straight line. Such a straight line represents the distribution of light amount without affection of any bright point 33 on the X-direction scan line in the detection area ($X_s$; $Y_s$). See FIG. 27C. The distribution of light amount shown by $\delta$ in FIG. 27C is represented by a curve obtained by scanning the pupil section in the X-direction.

The straight line connecting the points a and b is provided by:

$$L = \{(L_b - L_a)/X_a\}XX + L_a \qquad (17).$$

The scanning in the direction parallel to the edge is adopted to reduce errors since the state of light beams is symmetrical in the direction parallel to the edge and since it is ideally considered that the distribution of light amount is uniform except the bright point.

Such scanning is performed throughout the detection area ($X_s$; $Y_s$) to provide a modified value without affection of the bright point 33. The value stored in the frame memory 36 with respect to the detection area ($X_s$; $Y_s$) is then replaced by such a modified value which in turn is re-stored in the frame memory 36 as a new modified image.

Figure 28A:
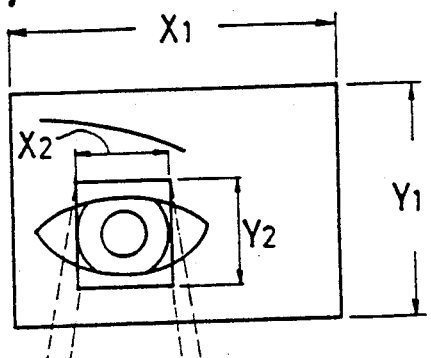
FIG. 28A is a view similar to FIG. 26B, showing one of eyes to be tested.
Figure 28B:
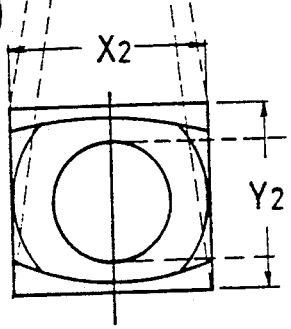
FIG. 28B is a view illustating a scanned area which includes the pupil of the eye to be tested.
Figure 28C:
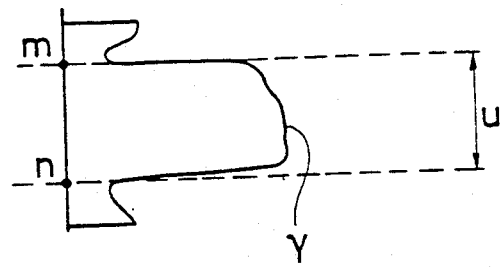
FIG. 28C is a view showing the distribution of light in a scan line which runs perpendicular to the edge.

The detection area is then enlarged into a size completely including the pupil of the eye to be tested (FIG. 28B). The enlarged detection area will be represented by ($X_2$; $Y_2$). With respect to the modified image, the enlarged detection area ($X_2$; $Y_2$) is scanned in a direction shown by Y, that is, a direction perpendicular to the edge so that the distribution of light amount can be obtained on the scanned line. The distribution of light amount γ on the Y-direction scanned line and particularly the scanned line passing through the bright point 33 as shown in FIG. 28C corresponds to the distribution shown in FIG. 10. This becomes a base for calculating the diopter value.

Figure 29:
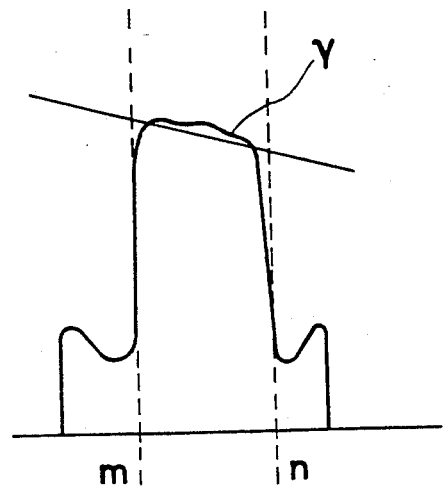
FIG. 29 illustrates an approximate gradient obtained from the distribution of light.

The gradient in the distribution of light amount γ can be determined by the use of various processes. For example, as shown in FIG. 29, a straight line is determined by the method of least squares to obtain its gradient.

Next, the diameter u of the pupil will be determined.

As shown in FIGS. 23A, 23B and 23C, the amount of light abruptly decreases at the iris out of the pupil portion (FIG. 28C). Thus, the rate of variation in the distribution of light amount includes peak values at boundary points m and n between the pupil 6 and the iris portion 34. Coordinates of these boundary points m and n can be read out from the frame memory and then processed by the processing unit 37 to determine the diameter u of the pupil.

If it is desired to determine only the pupil's diameter u, the elimination of the affection due to the bright point 33 is not particularly required. Since the bright point 33 is located at the center of the pupil 6, the boundary points m and n of the pupil appear as two peak points at which the rate of variation increase abruptly near the bright point. As described, these boundary points can be read out from the frame memory and then processed by the processing unit 37 to determine the pupil's diameter u. The determined diameter u of the pupil can be then displayed on the display 24. When the aforementioned equation (9) is used based on the detected diameter u of the pupil, the diopter of the eye to be tested can be calculated precisely.

It has been already described that the pupil's diameter u is one of the factors on measurement of the ocular refracting power in accordance with the present invention. The method of determining the pupil's diameter u also has been described above. A further embodiment of the present invention will now be described which can determine the pupil's diameter u while at the same time correcting the determined diameter u of the pupil into a predetermined value to facilitate the process of determining the ocular refracting power.

The correction of the pupil's diameter u will now be described with reference to FIG. 30.

Figure 30:
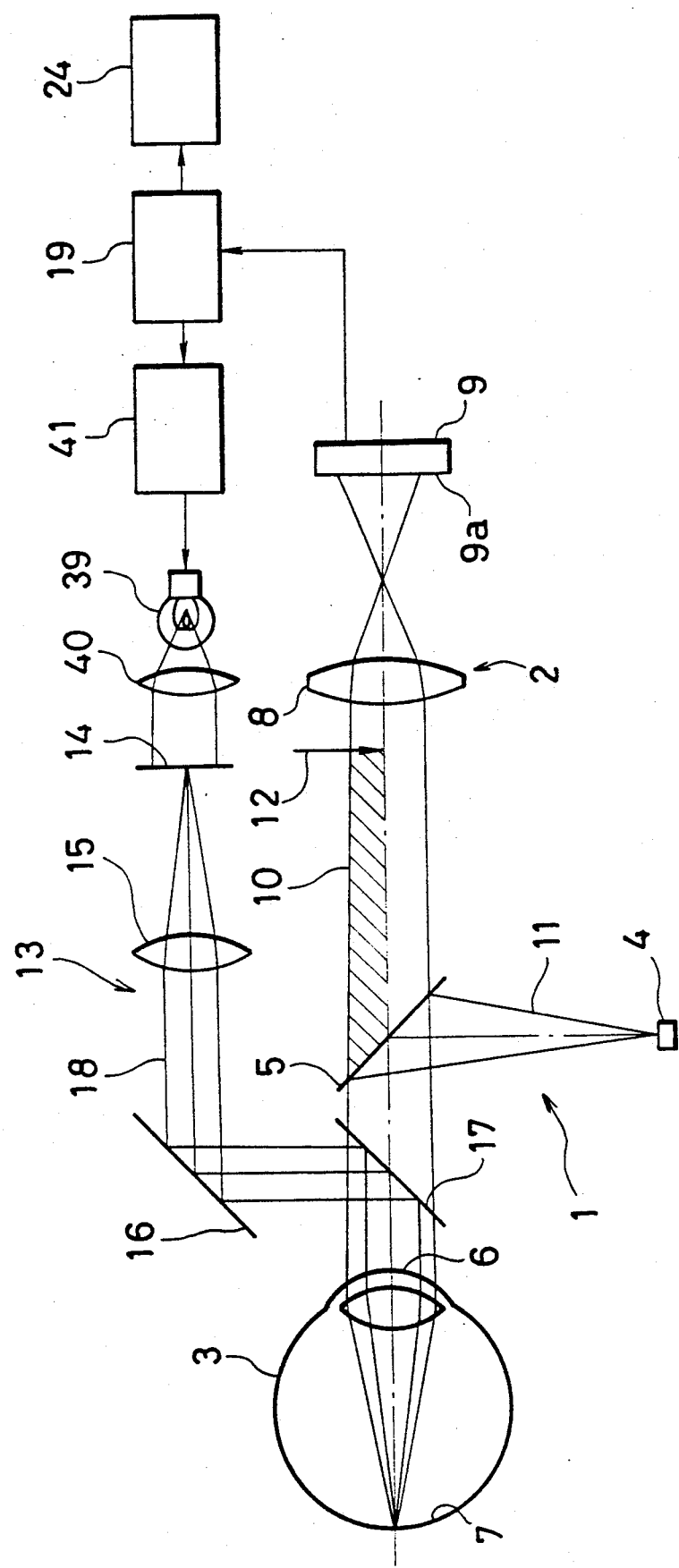
FIG. 30 is a view showing the basic arrangement of a further embodiment of an ocular refracting power measuring system according to the present invention.

FIG. 30 shows an arrangement comprising the arrangement shown in FIG. 1A added by a source of light 39 for illuminating a target to be watched 14 and a condenser lens 40. Brightness in the light source 39 can be regulated by a light regulator 41.

In order to correct the pupil's diameter u, the pupil's diameter u is first determined from the distribution of light amount. The amount of light in the light source 39 is then adjusted such that the determined diameter u of the pupil becomes coincide with a desired diameter $u_0$ of the pupil which has been previously set in the control section 38.

The process of determining the pupil's diameter u will be omitted herein since it has been already described.

It is further preferred that the scan is made in the horizontal direction to reduce the affection due to the cilia.

After the pupil's diameter u has been determined and if any deviation between the determined diameter u of the pupil and the desired diameter $u_0$ is detected by the processing unit 37, a command for correcting such a deviation is applied to the light regulator 41 which in turn functions to increase or decrease the amount of light in the illumination light source.

In response to the increase or decrease of the amount of light, the iris 34 of the eye to be tested increases or decreases to widen or contract the pupil's diameter u. As a result, the pupil's diameter u on measurement becomes coincide with the desired diameter $u_0$ of the pupil.

The value of the detected diameter of the pupil may be displayed such that the amount of light can be manually adjusted to cause this value to be coincide with the desired diameter $u_0$ of the pupil.

In such a manner, a diopter can be determined by the equation (10) as the pupil's diameter u is determined. If the diopter is corrected into a predetermined value by the use of the aforementioned process, however, the pupil's diameter u can be handled as constant in the equation (10). Therefore, the diopter can be determined immediately without consideration for any difference between pupil's diameters of individual persons and any circumstances on measurement.

Figure 31:
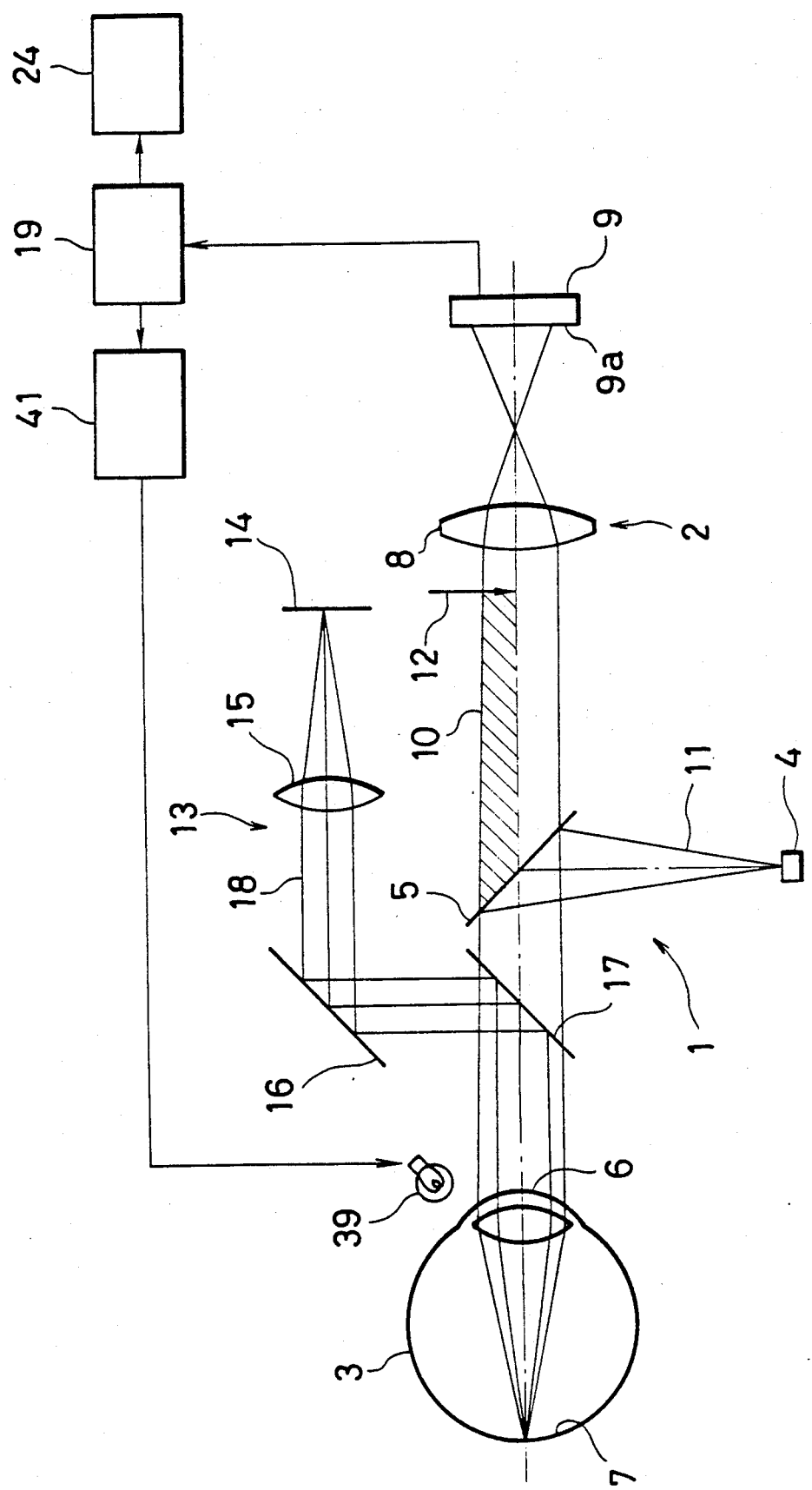
FIG. 31 is a view showing the basic arrangement of a further embodiment of an ocular refracting power measuring system according to the present invention.

The correction of the pupil's diameter may be accomplished by such an arrangement as shown in FIG. 31, in which the forward root of an eye to be tested is illuminated directly by a light source 39.

Figure 32:
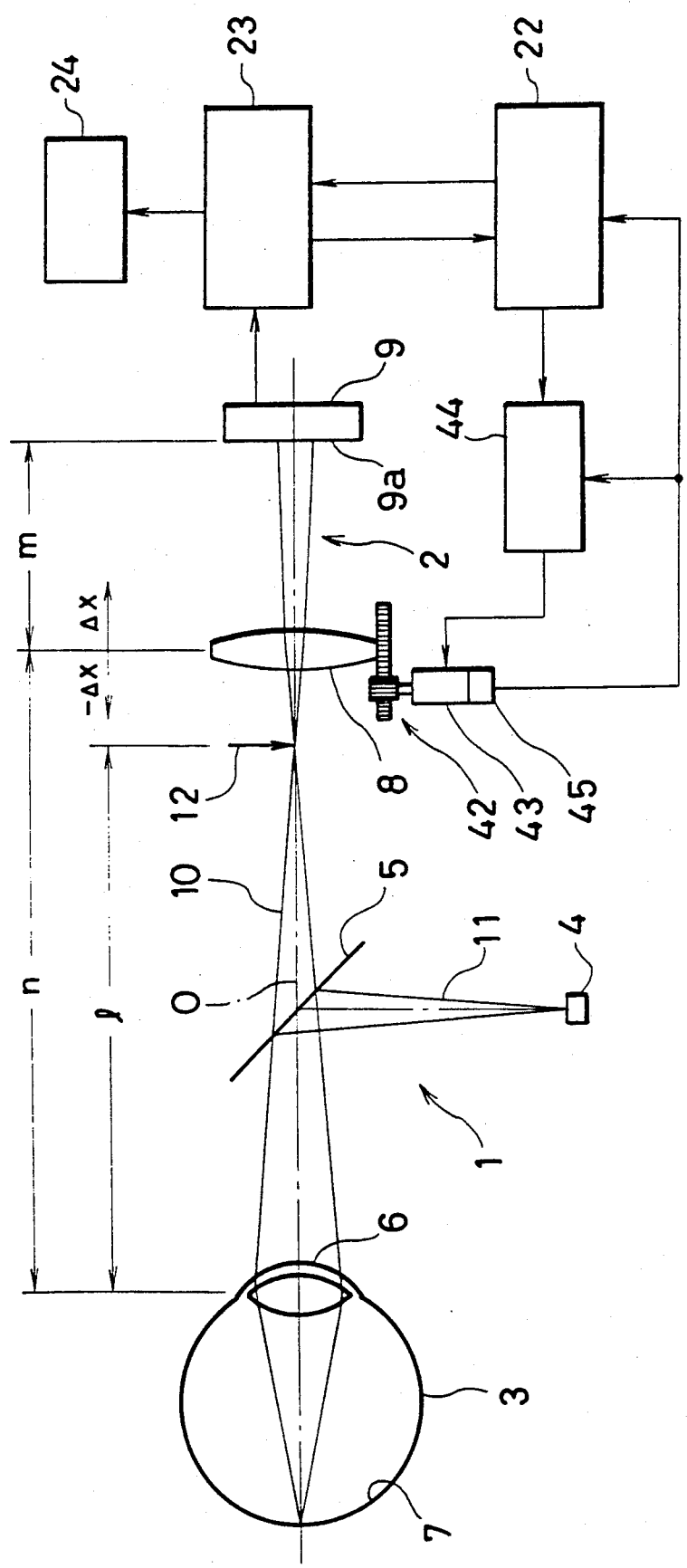
FIG. 32 is a view showing the basic arrangement of a further embodiment of an ocular refracting power measuring system according to the present invention.

The focusing function of the present invention will now be described with reference to FIG. 32.

The photo-refraction type ocular refracting power measuring system constructed in accordance with the present invention requires to focus an image. A further embodiment which will be described below assures that an objective lens is movable to make the focusing rapidly while reducing errors with increased accuracy.

The same parts as those of FIGS. 1 and 2 are respectively designated by the same reference numerals.

The objective lens 8 is supported for movement in a direction parallel to the optical axis and adapted to be driven as by a pulse motor 43 through a drive mechanism 42 such as rack-and-pinion mechanism or nut-screw mechanism.

The light receiving element 9 is connected with a processor section 23 for processing signals from the light receiving element 9. The processor section 23 is then connected with a main control section 22 which in turn is connected with a drive control section 44. The pulse motor 43 is controlled by the drive control section 44 and includes a rotation detector 45 such as encoder attached thereto. Detection signals from the rotation detector 45 are fed back to the drive control section 44. The processor section 23 also is connected with the display 24 such that the results from the processor section 23 will be displayed thereon.

The aforementioned adjustment of imaging the pupil of an eye to be tested on the light receiving element 9 will be made as follows.

If an image is unfocused onto the light receiving element 9, it is processed by the processing unit 23 with the resulting signal being then supplied to the main control section 22. Based on such a signal from the processing unit 23, the main control section 22 generates a drive command signal which in turn is applied to the drive control section 44. As received the drive command signal, the drive control section 44 energizes the pulse motor 43 to move the objective lens 8 in either of directions x or −x. The movement of the pulse motor 43 and thus the objective lens 8 is detected by the rotation detector 45 and then fed back to the drive control section 44. In such manner, the coincidence of the movement of the pulse motor 43 with the drive signal can be attained.

As the objective lens 8 is moved for the present position of the pupil 6, the relative position between the pupil 6, the light blocking member 12, the objective lens 8 and the light receiving element 9 becomes different from the reference relative position as described hereinbefore.

Since the deviation $\Delta D$ in the diopter relates to the distance l between the light source 4 (that is, the light blocking member 12) and the pupil 6 of the eye to be tested and the magnification $\beta$ as described, however, the aforementioned equation (10) should be corrected.

The correction will be described below.

It is now assumed that when the objective lens 8 is located at the reference position $x=0$, the image of the pupil 6 disposed at the reference position spaced away from the light blocking member 12 by a distance l will be imaged on the light receiving face 9a with a magnification $\beta$. At such a case, if the focal length of the objective lens 8 is f, the distance $m_1$ between the objective lens 8 and the light receiving face 9a is equal to $J(1+\beta)$.

If the eye to be tested has been shifted out of a proper position and when the objective lens 8 is moved by a distance $\Delta x$ to image the pupil on the light receiving face 9a, the distance $m_2$ between the light receiving face 9a and the objective lens 8 can be represented by the following equation:

$$m_2 = m_1 - \Delta x = J(1+\beta) - \Delta x \qquad (18)$$

If the magnification is changed to after the objective lens has been moved, this distance $m_2$ becomes $J(1+\beta')$. Thus, the equation (18) becomes:

$$J(1+\beta) - \Delta x = J(1+\beta 40) \qquad (19)$$

From this equation (19), the magnification $\beta'$ after the objective lens 8 has been moved by $\Delta x$ is:

$$\beta' = \beta - \Delta x/f \qquad (20)$$

There will now be considered the distance $l'$ between the eye to be tested and the light blocking member 12 (and thus the light source 4) after the objective lens 8 has been moved by the distance $\Delta x$ to image the pupil 6 onto the light receiving face 9a.

After the objective lens 8 has been moved, there is the following relationship between a variation $\Delta l$ in the distance between the light blocking member 12 and the eye to be tested 3, a variation $\Delta m$ in the distance between the light blocking member 12 and the objective lens 8 and a variation $\Delta n$ in the distance between the eye to be tested 3 and the objective lens 8:

$$\Delta n = \Delta l + \Delta m \qquad (21)$$

where $\Delta m$ is the movement of the lens and represented by:

$$\Delta m = \Delta x \qquad (22)$$

With the magnification $\beta$, the distance between the objective lens 8 and the eye to be tested 3 is $f(1+f/\beta)$.

When the magnification becomes $\beta'$ after the objective lens 8 has been moved by $\Delta x$, the above distance becomes equal to $f(1+f/\beta')$. Then, $\Delta n$ becomes:

$$\Delta n = f(1+f/\beta') - f(1+f/\beta).$$

By placing the above equation (20) into this modified equation, $$\Delta n = \Delta x/(\beta - \Delta x/f)\beta \qquad (23).$$

Thus, from the equations (21) to (23), $$\Delta l = \Delta n - \Delta m = \Delta x/(\beta - \Delta x/\beta) - \Delta x \qquad (24).$$

Therefore, the distance $l_x$ between the eye to be tested 3 and the light blocking member 12 after the objective lens 8 has been moved by the distance x becomes:

$$l_x = l + \Delta l = l + \Delta x/(\beta - \Delta x/f)\beta - \Delta x \qquad (25).$$

Being attended with the movement of the objective lens 8, the reference diopter $D_0$ will be changed to:

$$\begin{aligned} D_0' &= D_0 + (-1000/l + \Delta l) - (-1000/l) \\ &= D_0 + 1000\Delta l/l(l + \Delta l). \end{aligned} \qquad (26)$$

Thus, the aforementioned equation (10) becomes:

$$D = k'(\Delta f/f_0) \qquad (10')$$

where $k'$ is $LD_0'/u$.

By the fact that the movement x of the objective lens 8 on focusing is fed from the rotation detector 45 back to the main control section 22, the equations (25) and (26) can be calculated to provide a result on which a proper deviation of diopter can be determined from the equation (10').

The resulting deviation of diopter will be converted into the diopter of the eye to be tested, which in turn will be displayed on the display 24.

Figure 33B:
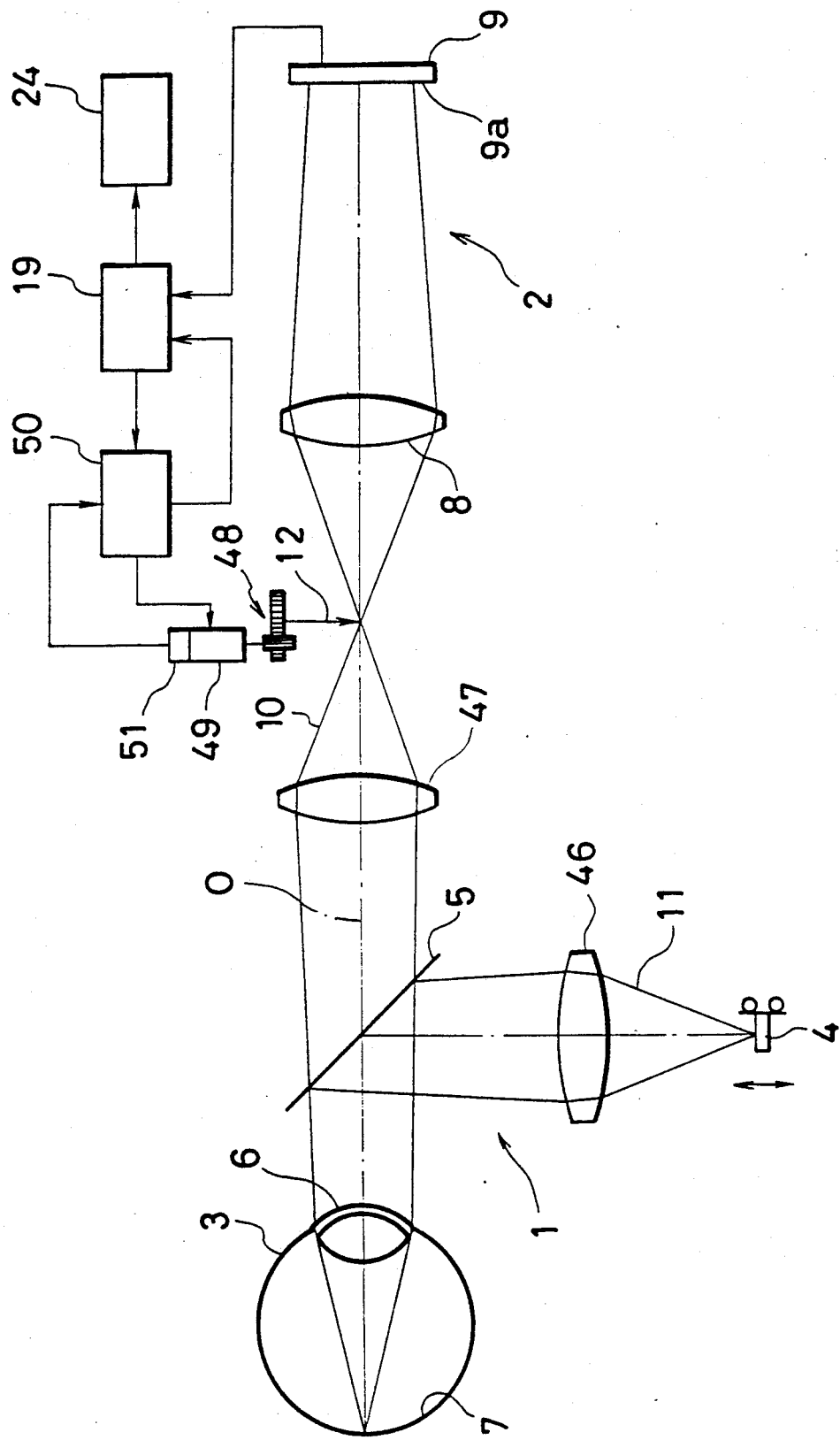
FIG. 33B is a view illustrating such a condition that the basic dioper is varied against FIG. 33A.

An ocular refracting power measuring system to which the present invention is applied and which can measure the ocular refracting power over a broader range is shown in FIGS. 33A and 33B.

Referring to FIGS. 33A and 33B, the ocular refracting power measuring system comprises a projector system 1 for projecting the image of a light source onto the eyeground 7 of an eye to be tested 3 and a light receiving system 2 for receiving a light beam 10 reflected from the eyeground 7. These systems 1 and 2 are disposed opposed to the eye to be tested 3.

The projector system 1 comprises a light source 4 movable along the optical axis in synchronism with a light blocking member 12 which will be described; a projecting lens 46 for condensing a light beam 11 from the light source 4; and a half-mirror 5 for reflecting the light beam 11 toward the eye to be tested 3. The projector system 1 is adapted to project the light beam 11 from the light source 4 onto the eyeground 7 through the pupil 6 to image the light source 4 thereon. The projector system 1 also is set such that the light source 4 can be focused on the eyeground 7 if the ocular refracting power of the eye to be tested 3 is equal to a reference diopter (that is, reference refracting power).

The light receiving system 2 comprises an objective lens 47 disposed opposed to the eye to be tested 3, a light blocking member 12, an imaging lens 8 and a light receiving element 9. The light beam 10 from the eyeground 7 is conducted onto the light receiving element 9 through the half-mirror 5. The light receiving face 9a of the light receiving element 9 is arranged at a position conjugate with the pupil 6 of the eye to be tested 3 about the imaging lens 8 and the objective lens 47. The light blocking member 12 is located within the optical path in the light receiving system 2 and can be moved by an actuator (e.g. pulse motor) 49 through a drive mechanism 48 along the optical axis of the light receiving system 2. The light blocking member 12 has an edge portion, the ridgeline of which is aligned with the optical axis O of the light receiving system 2 to block one-half of the light beam 10 about the optical axis O. The ridgeline of the edge portion is located at a position conjugate with the light source 4 about the half-mirror 5. The arrangement is such that the eyeground 7 can be focused and imaged on the light blocking member 12 when the ocular refracting power of the eye to be tested is equal to the reference diopter.

The ocular refracting power measuring system also comprises an ocular refracting power judging section 19 connected with a controller 50 for controlling the light receiving element 9 and the actuator 49.

As described previously, the ocular refracting power judging section 19 is adapted to calculate the diopter from the light receiving condition and the distribution of light amount in the light receiving element 9, with the result thereof being then displayed on a display 24. At least two different reference diopters have been pre-set in the ocular refracting power measuring section 19. Depending on the diopter in the eye to be tested 3, one of these different reference diopters can be selected to generate a command signal toward the controller 50. Depending on such a command signal, the controller 50 drives the actuator 49 to move the light blocking member 12 through the drive mechanism in such a direction as be indicated by the command signal. This position of the light blocking member 12 corresponds to one of the reference diopters. For example, if two reference diopters are set on measurement, one of two positions corresponding to one of the two reference diopters will be selected.

The movement (position) of the light blocking member 12 is detected by means of a detector 51 such as encoder and then inputted to the controller 50 which in turn functions to supply the position of the light blocking member 12 back to the ocular refracting power judging section 19.

FIG. 33A shows the light blocking member 12 and the light source 4 at their positions taken, for example, when the reference diopter $D_0$ is equal to minus three ($-3$) while FIG. 33B shows the light blocking member 12 and the light source 4 at their positions, for example, when the reference diopter $D_0$ is equal to three (3).

After the reference diopter has been set, the measurement of the ocular refracting power has been described previously and will be omitted herein.

The ocular refracting power measuring system should be conditioned such that the eye to be tested is aligned with the optical axis of the camera to provide measurements with improved accuracy. However, the conventional ocular refracting power measuring systems were adapted to judge the orientation of an eye to be tested in an infant.

Figure 34A:
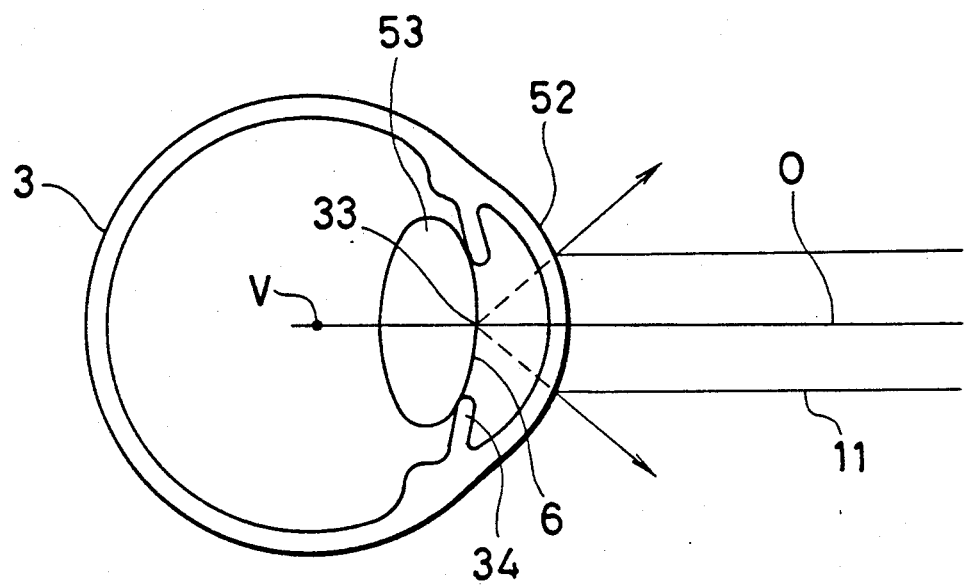
FIGS. 34A and 34B illustrating the relationship between the optical axis and a bright point in an eye to be tested.
Figure 34B:
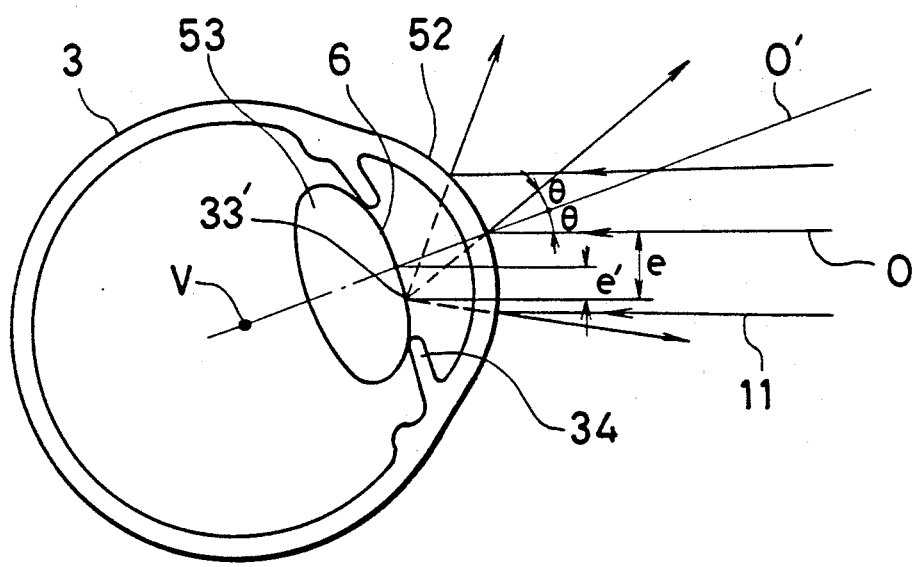

FIGS. 34A and 34B illustrate some examples to which the present invention is embodied. In these embodiments, the orientation of an eye to be tested is judged from the distribution of light amount obtained by the CCD camera. Under a proper orientation, the ocular refracting power is determined from the distribution of light amount. Thus, any unnatural error can be prevented from creating on measurement.

More concretely, the boundary points m and n between the bright point 33 and the pupil 6 are determined from such a variation of light amount as shown in FIG. 23C under such a distribution of light amount. From the position of the bright point 33 and the boundary points m, n, the diameter u of the pupil will be determined to specify the position of the eye to be tested.

If the eye to be tested is oriented just forward, the bright point 33 is at the center of the pupil 6. Therefore, the position of the eye to be tested can be specified by judging the positional relationship between the bright point 33 and the boundary points m, n.

The relationship between the position of the eye to be tested and the bright point 33 will be described with reference to FIGS. 34A and 34B.

In FIGS. 34A and 34B, V is a central point for rotation in the eyeball.

FIG. 34A shows such a state under which the viewing axis of the eye to be tested 3 is aligned with the optical axis O. The light beam 11 is reflected by the cornea 52 to form the virtual image 33 of the light source on the optical axis O, this virtual image being the aforementioned bright point. If the eye to be tested 3 is rotated about the central point V by an angle $\theta$ as shown in FIG. 34B, the viewing axis O' of the eye to be tested 3 will be shifted from the optical axis O similarly by the angle $\theta$. At this time, the virtual image 33' formed by the light beam which has been reflected by the cornea 52 will be shifted relative to the optical axis O by e and relative to the pupil 6 by e'.

If it is detected whether or not the bright point 33 is on the center of the pupil 6, it can be judged whether or not the viewing axis O' of the eye to be tested is aligned with the optical axis O of the optical system. In FIGS. 34A and 34B, reference numeral 53 denotes the crystalline lens.

As shown in FIGS. 23A, 23B and 23C, the amount of light abruptly decreases at the iris portion out of the pupil portion (FIG. 28C). The rate of variation in the distribution of light amount $\gamma$ will provide peak values at the boundary points m and n between the pupil 6 and the iris portion 34. The coordinates of the boundary points m and n can be read out from said frame memory and processed by the processing unit 37 to determine the pupil's diameter u and the center of the pupil.

The boundary points m and n can be determined independently of the position of the edge in the light blocking member 12. If the scan line is run in a direction parallel to the edge to determine the boundary points m and n from the resulting distribution of light amount, it is convenient since measurements will not be affected by the edge or cilia.

The processing unit 37 then compares the central position of the pupil thus calculated with the position of the bright point 33 which has been previously determined. If these positions are coincide with each other or the difference therebetween is within a predetermined range, it is judged that the eye to be tested 3 is oriented just forward. This result is displayed on the display 24. The operator can execute the measurement while viewing the display 24. As a result, the measurement can be performed at the desired time judged to be proper.

The judgement may be fed back to the control section 38 which in turn causes an image for measuring the ocular refracting power to store in the frame memory 36 at a proper time. The distribution of light amount thus obtained may be then used to measure the ocular refracting power. This means that the measurement of ocular refracting power can be automated.

Although it has been judged whether or not the bright point 33 is at the center of the pupil 6 in the above embodiment, it may be similarly judged whether or not the viewing axis of the eye to be tested is aligned with the optical axis of the system by determining whether or not the bright point 33 is at the center of the iris. As seen from FIG. 23B, a remarkable variation of light amount exists also at the boundary of the iris 34. By determining such a remarkable variation of light amount, the diameter and central position of the iris 34 can be determined. When the central position of the iris 34 is compared with the position of the bright point 33, the viewing axis can be determined.

If part of the cilia overlaps the iris 34 or pupil 6, it is preferred that the distribution of light amount is determined on a plurality of scan lines parallel to the X-direction in which the cilia may provide less influence. From the distribution of light amount thus obtained, the boundary between the iris 34 and the pupil 6 may be determined to calculate a circle (ellipse) therefrom so that the diameters and centers of the iris and pupil will be determined from the calculated results.

Furthermore, such judgements of the viewing axis may be utilized to measure any abnormal attitude in the eyeball, such as strabismus, heterophoria or the like.

In FIG. 1A, a person to be tested is forced to view a target to be watched with both his eyes. Under such a condition that the optical axes of the eyes to be tested are stationary, the viewing axes of the eyes are determined with respect to their directions.

If the viewing axes of the eyes are oriented just forward as described, each of the bright points 33 will be substantially at the center of each of the pupils 6. By determining the positional relationship between each of the bright points 33 and the boundary points m and n between that pupil 6 and the corresponding iris, the viewing axis thereof can be substantially specified.

Strabismus means that the optical axes of both eyes are oriented to different directions. Thus, strabismus can be judged by detecting the viewing directions of both the eyes. The degree of strabismus may be determined by measuring both the eyes to be tested with respect to deviation e' between the bright point 33 and the center of the pupil 6 and determining a difference between the deviations e'.

The deviations $e_R'$ and $e_L'$ are compared with each other. If both the deviations $e_R'$ and $e_L'$ are equal to zero, it is judged that the eyes to be tested are normal. If $\tau = e_R' - e_L'$ is beyond a predetermined level, it is judged that the eyes to be tested are strabismus. The degree of strabismus can be judged from the magnitude of the value $\tau$.

If at least one of the eyes to be tested has its deviation e' equal to zero or less than a predetermined level, it is judged that the eyes to be tested 3 are oriented just forward.

Results from the judgements of the value $\tau$ and viewing direction are displayed on the display 14. Thus, the operator can visually confirms whether or not the patient's eyes are strabismus and how degree the strabismus belongs to and which direction the deviation e' is shifted, while at the same time confirming the viewing directions of the patient's eyes.

Figure 35:
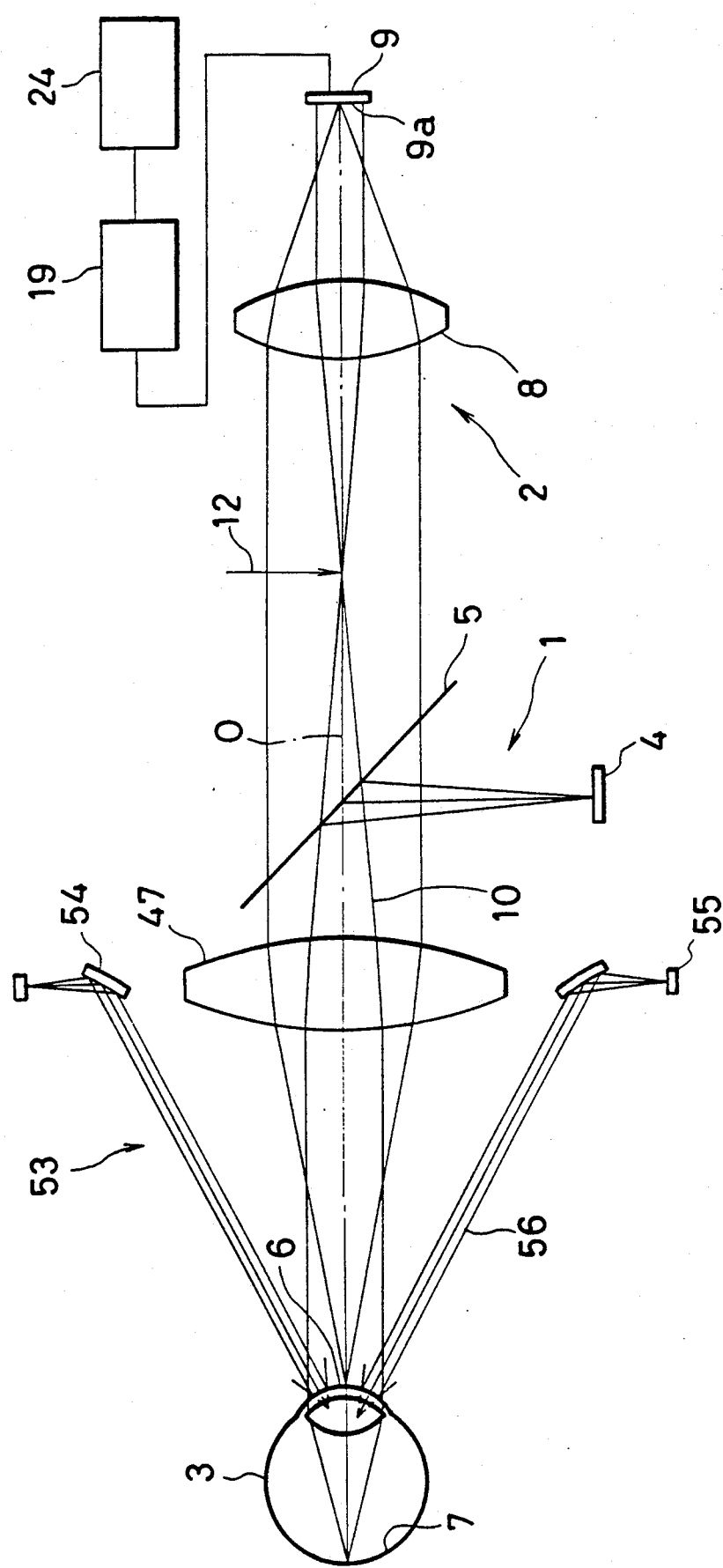
FIG. 35 is a view showing the basic arrangment of a further embodiment of an ocular refracting power measuring system according to the present invention.

FIG. 35 shows a further embodiment of the present invention which can measure the shape of the cornea of an eye to be tested.

Referring to FIG. 35, the ocular refracting power measuring system comprises an ocular refracting power measuring projector system 1 for projecting the image of a light source onto the eyeground 7 of an eye to be tested; a light receiving system 2 for receiving a light beam 10 reflected from the eyeground 7; and a cornea shape measuring projector system 53 for projecting an index beam onto the eye to be tested 3. The ocular refracting power measuring projector system 1 and the light receiving system 2 are disposed opposed to the eye to be tested 3. The cornea shape measuring projector system 53 has an optical axis shared with the ocular refracting power measuring projector system 1 and is arranged around the ocular refracting power measuring projector system 1.

The ocular refracting power measuring projector system 1 comprise a light source 4 and a half-mirror 5 for reflecting a light beam 11 from the light source 4 toward the eye to be tested 3. The projector system 1 is adapted to project the light beam 11 from the light source 4 onto the eyeground 7 through the pupil 6 via the objective lens 47 to image the light source 4 thereon. In the projector system 1, the distance between the eyeground 7 and the eye to be tested 3 is so set that the image of the light source 4 can be focused on the eyeground 7 if the refracting power of the eye to be tested 3 is a reference diopter (reference refracting power).

The light receiving system 2 comprises an objective lens 47, a relay lens 8 and a light receiving element 9. The arrangement is such that the light beam 10 from the eyeground 7 is conducted onto the light receiving element 9 through the half-mirror 5.

The light receiving face 9a of the light receiving element 9 is disposed at a position conjugate with the pupil 6 of the eye to be tested 3 about the objective lens 47 and the relay lens 8.

Within the optical path of the light receiving element 2, an edge-like light blocking member 12 is disposed at a position conjugate with the light source 4 about the half-mirror 5. The light blocking member 12 is adapted to block one-half of the light beam 10 about the optical axis of the relay lens 8.

The cornea shape measuring projector system 53 comprises a ring-like mirror (cylindrical mirror) 54 disposed to have its optical axis shared with the optical axis O and a ring-like light source 55 disposed concentrically of the ring-like mirror 54 and adapted to emit an index light beam 56. The index light beam 56 emitted from the ring-like light source 55 is reflected by the ring-like mirror 54 to form ring-shaped index rays parallel to one another which in turn are projected onto the cornea.

In this embodiment, both the images used to measure the cornea configuration and the ocular refracting power are conducted to the same light receiving element 9. However, another half-mirror may be disposed behind the relay lens 8 such that these images can be conducted to different light receiving elements, respectively.

Where it is wanted to measure the ocular refracting power, the light source 4 is first lighted on while the light source 55 is lighted off. The measurement of the ocular refracting power has been described previously and will be omitted herein.

Figure 36:
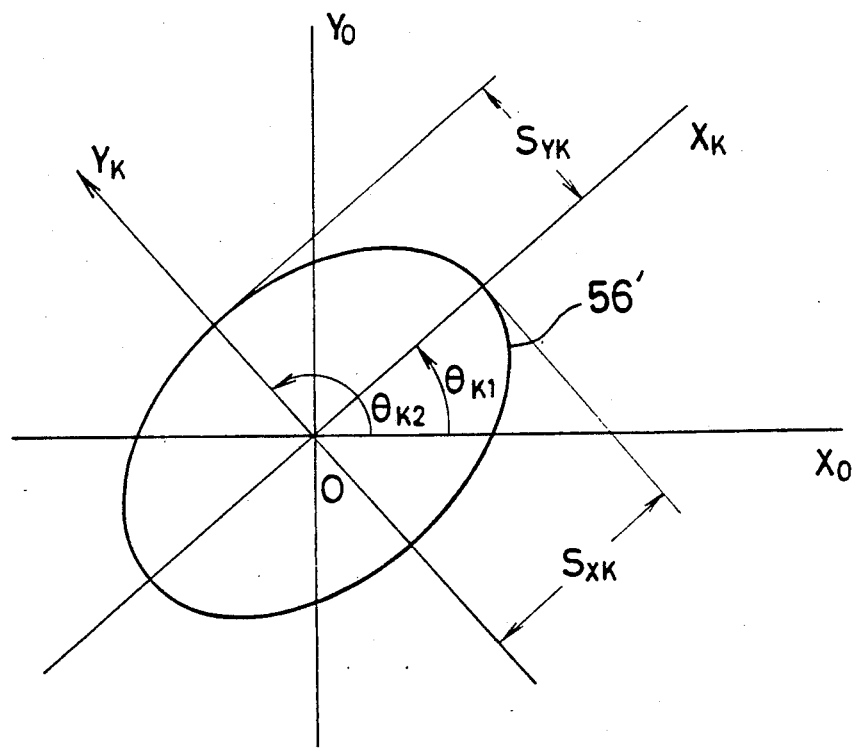
FIG. 36 is a view illustrating the shape of a ring-like index beam which is projected onto the light receiving surface.

The measurement of the configuration of cornea will now be described with reference to FIG. 36.

The light source 4 is lighted off while the ring-like light source 55 is lighted on. Ring-like index light beam 56 from the ring-like light source 55 is projected onto the cornea through the ring-like mirror 54. The index light beam projected on the cornea is reflected from the cornea and also images a virtual image within the cornea. Therefore, the shape of the index light beam projected onto the cornea may be viewed by signals from the light receiving element 9.

If the cornea is of a perfect sphere, the index light beam forms a true circle on the light receiving element 9. If not, the index beam forms an ellipse 56' on the light receiving element 9, as shown in FIG. 36.

The ellipse may be calculated by sequentially determining coordinates on pixels on the light receiving element 9, which receive the index beam.

It is assumed herein that the reference coordinate system on the light receiving element 9 has ($X_0-Y_0$) and that the longer axis of the calculated ellipse is $X_K$-axis and the shorter axis thereof is $Y_K$-axis.

The radius $S_{XK}$ of the longer axis ($X_K$) in the ellipse 56' corresponds to the radius of curvature $R_1$ of the weak main radial line of the cornea C while the radius $S_{YK}$ of the shorter axis ($Y_K$-axis) corresponds to the radius of curvature $R_2$ of the strong main radial line of the same cornea. The angles $\theta_{K1}$ and $\theta_{K2}$ of the longer and shorter axes correspond to the angles $\theta_1$ and $\theta_2$ of the strong and weak main radial lines, respectively.

The general formula of the ellipse 56' in the $X_K-Y_K$ coordinate system is represented by:

$$Ax^2 + By^2 + C_{XY} = 1 \quad (27);$$

$$A = \cos^2\theta_{K1}/(2S_{XK})^2 + \sin^2\theta_{K1}/(2S_{YK})^2$$

$$B = \sin^2\theta_{K1}/(2S_{XK})^2 + \cos^2\theta_{K1}/(2S_{YK})^2$$

$$C = 2\sin\theta_{K1}\cos\theta_{K1}/(2S_{XK})^2 - 2\sin\theta_{K1}\cos\theta_{K1}/(2S_{YK})^2 \quad (28).$$

The radius $S_K$ of the ellipse 56' is represented by the following relationship:

$$S_K = Y X \beta$$

$$Y = hXr/2 \quad (29)$$

where r is the radius of the cornea; h is the radius of a true circle as reference; and X is the magnification of the entire optical system.

Form the equations (27) and (28), the values $S_{XK}$ and $S_{YK}$ are determined. From the equation (29), the radius of curvature $r_1$ of the weak main radial line is:

$$r_1 = 2S_{XK}/\beta \cdot h \quad (30).$$

The radius of curvature $r_2$ of the strong main radial line is similarly:

$$r_2 = 2S_{YK} \cdot Z/\beta \cdot h \quad (31).$$

Furthermore, it can be determined that the angle of the strong main radial line $\theta_1$ is equal to $\theta_{K2}$ while the angle of the weak main radial line $\theta_2$ is equal to $\theta_{K1}$.

What is claimed is:

1. An ocular refracting power measuring system comprising a projector system for projecting the image of a light source on the eyeground of an eye to be tested, a light receiving element, a light receiving system for condensing the light beam from said eyeground onto said light receiving element disposed at a position substantially conjugate with the pupil of said eye to be tested, an edge-like light blocking member disposed at a position substantially conjugate with said light source for blocking part of a light beam reflected from the eyeground, a circuit measuring the ocular refracting power of said eye to be tested based on the distribution of light amount on said light receiving element.

2. An ocular refracting power measuring system as defined in claim 1 wherein the light source in said projector system has such a size as extends partially across the blocking boundary line of said light blocking member.

3. An ocular refracting power measuring system as defined in claim 2 wherein said light blocking member has a linear light blocking boundary line located within a plane perpendicular to the optical axis of said light receiving system and said light blocking member blocks one-half of said light beam about the optical axis of said light receiving system.

4. An ocular refracting power measuring system as defined in claim 3 wherein said slit-shaped measuring light source is symmetrical relative to the light blocking boundary line.

5. An ocular refracting power measuring system as defined in claim 2 wherein the measuring light source is of a slit shape which extends in a direction perpendicular to the linear light blocking boundary line of said light blocking member.

6. An ocular refracting power measuring system as defined in claim 1, further comprising another projector system for projecting the image of an invisible light source onto the eyeground of said eye to be tested and a target watching system for projecting a light beam from a target to be watched onto said eye to be tested.

7. An ocular refracting power measuring system as defined in claim 6 wherein the light beam from the target to be watched is irradiated toward said eye to be tested through a dichroic mirror which is disposed on the optical axis of said ocular refracting power measuring system.

8. An ocular refracting power measuring system as defined in claim 1, further comprising an edge-like light blocking member disposed in the optical path of said light receiving system such that said light blocking member is rotatable about the optical axis of said light receiving system within a plane perpendicular to said optical axis, said light blocking member having at least three rotated positions at each of which a distribution of light amount on said light receiving element can be measured to determine the ocular refracting power.

9. An ocular refracting power measuring system as defined in claim 1 wherein said projector system includes light source means comprising a plurality of light source portions, said light source portions being disposed within a plane perpendicular to the optical axis and on different radial lines about said optical axis and selectively lighted on and wherein a light blocking member is disposed on the optical path of said light receiving system in a plane perpendicular to the optical axis thereof, said light blocking member having an edge-shaped ridgeline extending relative to said plurality of light source portions in a direction perpendicular to at least three radial directions about said optical axis.

10. An ocular refracting power measuring system as defined in claim 1 wherein said projector system includes light source means comprising a plurality of light source portions, said light source portions being disposed within a plane perpendicular to the optical axis and on different radial lines about said optical axis and selectively lighted on and wherein a light blocking member and beam diverging means are disposed on the optical path of said light receiving system in a plane perpendicular to the optical axis thereof, said light blocking member having an edge-shaped ridgeline extending relative to said plurality of light source portions in a direction perpendicular to at least three radial directions about said optical axis, said beam diverging means being adapted to separate light beams passed through said edge-shaped ridgeline from one another and to conduct these separated light beams toward a photoconductive element.

11. An ocular refracting power measuring system as defined in claim 1, further comprising a processor section for calculating the spherical curvature, degree of astigmatism and astigmatic axis of an eye to be tested from information of the distributions of light amount on said light receiving element in at least two directions when said light blocking member is disposed relative to said eye to be tested in a predetermined radial direction and from information of the distributions of light amount on said light receiving element in at least two directions when said light blocking member is disposed in another radial direction different from said radial direction.

12. An ocular refracting power measuring system as defined in claim 11, further comprising an edge-shaped light blocking member for blocking part of the light beam reflected from the eyeground of said eye to be tested in at least two radial directions.

13. An ocular refracting power measuring system as defined in claim 1, further comprising a processor section for determining the image of a bright point created by the reflection at the cornea of said eye to be tested, based on image signals from said light receiving element.

14. An ocular refracting power measuring system as defined in claim 13 wherein the position of a bright point formed by the reflection at the cornea of the eye to be tested is determined from the image of said light receiving element and at the same time the center of said eye to be tested is determined from the distribution of light amount on said image and wherein the center of said eye to be tested is compared with the position of the bright point to determine the viewing direction in the eye to be tested.

15. An ocular refracting power measuring system as defined in claim 13 wherein the center of the image of a bright point formed by the light beam reflected from the cornea of each eye to be tested and a deviation between said center of the image and the center of the image of the pupil in each eye to be tested are determined about both the eyes to measure an abnormality about the positions of the eyes to be tested.

16. An ocular refracting power measuring system as defined in claim 1, further comprising a processor section for erasing the image of a bright point created by the reflection at the cornea of said eye to be tested, based on image signals from said light receiving element.

17. An ocular refracting power measuring system as defined in claim 16, at least comprising a frame memory for storing an image on said light receiving element and a processor section for calculating the erasure of a bright point based on data stored in said frame memory, whereby a distribution of light amount can be determined on a line passing through said bright point in the image of said light receiving element and a peak part in the distribution of light amount at which the amount of light increases abruptly can be erased.

18. An ocular refracting power measuring system as defined in claim 16 at least comprising a frame memory for storing an image on said light receiving element and a processor section for calculating the erasure of a bright point based on data stored in said frame memory and wherein the image of said light receiving element is scanned about a given area in a direction parallel to said edge, a distribution of light amount is determined on each of the scan lines, a peak part in the distribution of light amount at which the amount of light increases abruptly is erased, said erased part being used to prepare a modified image from a modified distribution of light amount approximated to a straight line, the image of said light receiving element being replaced by said modified image.

19. An ocular refracting power measuring system as defined in claim 1 wherein ocular refracting powers are measured at two opposed positions at which said light blocking member is located and wherein measurements at both the two positions are averaged.

20. An ocular refracting power measuring system as defined in claim 19 wherein ocular refracting powers are measured about each of at least two radial lines at two opposed positions at which said light blocking member is located and wherein measurements about each of said two radial lines are averaged.

21. An ocular refracting power measuring system as defined in claim 1, further comprising a processor section for determining the diameter of the pupil of said eye to be tested, based on signals from said light receiving element.

22. An ocular refracting power measuring system as defined in claim 21, further comprising a processor section for calculating the diameter of the pupil based on image signals from said light receiving element and wherein the calculated diameter of the pupil is caused to be coincide with a desired value which is set by adjusting the amount of light in a light source for regulating the diameter of the pupil.

23. An ocular refracting power measuring system as defined in claim 1 wherein said light receiving system further includes an objective lens for condensing the light beam from said eyeground onto said light receiving element, said objective lens being movable along the optical axis, the movement of said objective lens causing the image of the pupil to be imaged on said light receiving element, whereby the ocular refracting power of the eye to be tested can be measured based on the movement of said objective lens and the distribution of the light beam projected onto said light receiving element.

24. An ocular refracting power measuring system as defined in claim 1 wherein said light receiving system comprises a first lens system disposed opposed to the eye to be tested, a light blocking member disposed behind said first lens system and adapted to block at leans a part of the reflected light beam and a second lens system for conducting the light beam passed through said light blocking member onto said light receiving element, said light blocking member being movable along the optical axis.

25. An ocular refracting power measuring system as defined in claim 1, further comprising a cornea shape measuring system for projecting an index light beam toward the cornea of an eye to be tested and determining the shape of said cornea from an index image which is formed by the index light beam reflected from said cornea.

26. An ocular refracting power measuring system as defined in claim 25 wherein the pupil's image of the eye to be tested and the index image are conducted onto the same light receiving element which in turn generates signals used to measure the ocular refracting power and the shape of the cornea in the eye to be tested.

* * * * *